(12) United States Patent
Sadeghpour et al.

(10) Patent No.: US 9,610,235 B2
(45) Date of Patent: Apr. 4, 2017

(54) METHODS AND COMPOSITIONS TO IMPROVE MECHANICAL RESISTANCE OF TEETH

(75) Inventors: Arman Sadeghpour, Metairie, LA (US); Tetsuo Nakamoto, Kenner, LA (US)

(73) Assignee: THEOCORP HOLDING CO., LLC, Metairie, LA (US)

(*) Notice: Subject to any disclaimer, the term of this patent is extended or adjusted under 35 U.S.C. 154(b) by 375 days.

(21) Appl. No.: 13/642,125

(22) PCT Filed: Feb. 14, 2011

(86) PCT No.: PCT/US2011/024734
§ 371 (c)(1),
(2), (4) Date: Feb. 11, 2013

(87) PCT Pub. No.: WO2011/100671
PCT Pub. Date: Aug. 18, 2011

(65) Prior Publication Data
US 2013/0129641 A1    May 23, 2013

Related U.S. Application Data

(60) Provisional application No. 61/303,774, filed on Feb. 12, 2010.

(51) Int. Cl.
| | |
|---|---|
| *A61K 8/49* | (2006.01) |
| *A61Q 11/00* | (2006.01) |
| *A61K 31/437* | (2006.01) |
| *A61K 31/52* | (2006.01) |
| *A61K 31/66* | (2006.01) |
| *A61K 33/06* | (2006.01) |
| *A61K 33/42* | (2006.01) |
| *A61K 45/06* | (2006.01) |
| *A61K 8/24* | (2006.01) |
| *A61K 8/365* | (2006.01) |
| *A61K 8/19* | (2006.01) |
| *A61K 8/21* | (2006.01) |

(52) U.S. Cl.
CPC .............. *A61K 8/4953* (2013.01); *A61K 8/19* (2013.01); *A61K 8/21* (2013.01); *A61K 8/24* (2013.01); *A61K 8/365* (2013.01); *A61K 31/437* (2013.01); *A61K 31/52* (2013.01); *A61K 31/66* (2013.01); *A61K 33/06* (2013.01); *A61K 33/42* (2013.01); *A61K 45/06* (2013.01); *A61Q 11/00* (2013.01)

(58) Field of Classification Search
USPC ............................................. 423/308; 424/52
See application file for complete search history.

(56) References Cited

U.S. PATENT DOCUMENTS

| | | | | |
|---|---|---|---|---|
| 5,571,502 | A | * | 11/1996 | Winston ................... A61K 8/19 424/49 |
| 5,626,838 | A | | 5/1997 | Cavanaugh, Jr. |
| 5,919,426 | A | * | 7/1999 | Nakamoto et al. ........... 423/308 |
| 6,693,104 | B2 | * | 2/2004 | Lee ........................ A23G 3/364 424/48 |
| 2004/0022747 | A1 | * | 2/2004 | Fisher et al. ..................... 424/52 |
| 2005/0054682 | A1 | | 3/2005 | Phillips |
| 2005/0152852 | A1 | | 7/2005 | Nishimura et al. |
| 2006/0189566 | A1 | | 8/2006 | Komatsu et al. |
| 2008/0214675 | A1 | | 9/2008 | Ley et al. |
| 2009/0087501 | A1 | | 4/2009 | Cummins |
| 2013/0129641 | A1 | | 5/2013 | Sadeghpour et al. |

FOREIGN PATENT DOCUMENTS

| | | | |
|---|---|---|---|
| EP | 2533786 A2 | 12/2012 | |
| JP | 2008-247870 | * 10/2008 | .......... A61K 31/353 |
| JP | 2010275261 A | 12/2010 | |
| NZ | 601989 A | 11/2014 | |
| WO | 2011/100671 A3 | 8/2011 | |

OTHER PUBLICATIONS

Janet Raloff, "Chocolate Constituent Bests Fluoride". Science News:Magazine of the Society for Science & the Public dated 5:14pm, May 22, 2007 (pp. 1-3).*
Supplementary European Search Report re European Patent Application No. 11742948 (May 13, 2015).
Vietnamese Substantive Examination Result, dated Jan. 27, 2015, issued in Application No. 1-2012-02518, and English translation thereof.

\* cited by examiner

*Primary Examiner* — Walter Webb
(74) *Attorney, Agent, or Firm* — McBee Moore Woodward & Vanik IP, LLC

(57) ABSTRACT

Provided are compositions and methods for preventing dental caries, as well as aqueous compositions and methods for improving the mechanical strength of teeth.

15 Claims, 13 Drawing Sheets

METHODS AND COMPOSITIONS TO IMPROVE MECHANICAL RESISTANCE OF TEETH

CROSS REFERENCE TO RELATED APPLICATIONS

This application is a §371 National Stage Application of PCT/US2011/024734, filed 14 Feb. 2011, which claims priority to U.S. Application 61/303,774 filed 12 Feb. 2010.

BACKGROUND

1. Field

The present application relates to compositions and methods for preventing dental caries. In particular, the present application relates to aqueous compositions and methods for improving the mechanical strength of teeth.

2. Description of Related Art

Dental caries are one of the most common preventable diseases plaguing humans and non-human animals worldwide. Dental caries (tooth decay, cavity) is caused by bacterial processes which damage hard tooth structure (e.g., enamel, dentin, and cementum). These tooth structures break down progressively, producing holes in teeth (dental caries). Two groups of bacteria—*Streptococcus mutans* and *Lactobacillus* spp.—produce lactic acid in the presence of fermentable carbohydrates such as sucrose, fructose, and glucose, and are largely responsible for initiating caries. Teeth, which are comprised primarily of minerals, are constantly subjected to demineralization and remineralization between teeth and the surrounding saliva. Hydroxylapatite—a crystalline calcium phosphate—is the primary mineral of a tooth's enamel surface and has the general formula $Ca_5(PO_4)_3(OH)$, but is usually written $Ca_{10}(PO_4)_6(OH)_2$, to denote that the crystal unit cell comprises two entities. When the pH at the tooth surface drops below 5.5, demineralization proceeds faster than remineralization (i.e. a net loss of hydroxylapatite on the tooth's surface occurs). This loss of mineral structure results in tooth decay. If left untreated, the disease can lead to pain, tooth loss, infection, and, in extreme cases, death.

To prevent dental caries, dental professionals recommend brushing teeth at least twice a day with a fluoride-containing dentifrice, which removes bacterial plaques. Fluoride assists in the prevention of caries by binding to hydroxylapatite surfaces in the tooth enamel, forming fluorapatite and making the enamel more resistant to demineralization (and thus more resistant to decay). Fluoride is also commonly added to municipal water supplies to prevent tooth decay, yet the National Research Council (functioning under the auspices of the National Academy of Sciences, the National Academy of Engineering, and the Institute of Medicine) recently concluded that the levels of fluoride found in municipal water supplies and the levels of fluoride known to cause toxic effects are dangerously close to one another.

There has been little to no innovation in commercial toothpastes since the mid-twentieth century. The active anti-caries ingredient in all commercial toothpastes is either 0.24% sodium fluoride (NaF, 0.15% w/v fluoride ion), or 0.76% sodium monofluorophosphate ($Na_2FPO_3$, 0.14% w/v fluoride ion). Recent innovations in the commercial toothpaste market are directed to flavors, abrasives, or whiteners, instead of cavity-fighting activity.

Theobromine (IUPAC name: 3,7-dimethyl-2,3,6,7-tetrahydro-1H-purine-2,6-dione; also known as 3,7-dimethylxanthine) is a white (or colorless) bitter-tasting crystalline powder with a sublimation point of 290-295° C., a melting point of 357° C., and a molecular weight of 180.16 g/mol. The solubility of theobromine in water is 1.0 g/2 L; in boiling water, it is 1.0 g/150 mL, and in 95% ethanol it is 1.0 g/2.2 L. Theobromine is related chemically to caffeine and theophylline, and is found in numerous foods including chocolate, cocoa, tea leaves, and acai berries. The chemical structures of theobromine, theophylline (1,3-dimethylxanthine), and caffeine (1,3,7-trimethylxanthine) are given below as formulae I, II, and III, respectively.

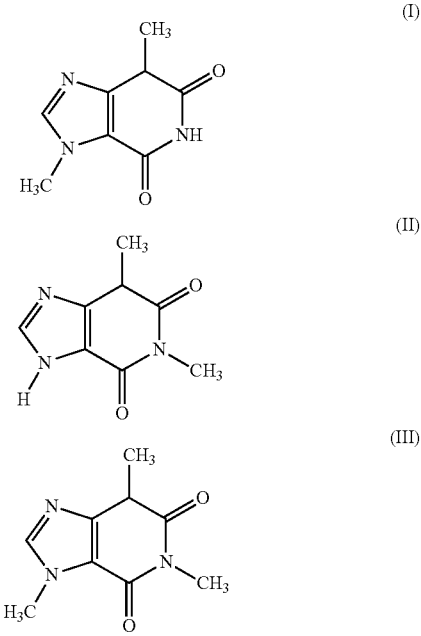

Theobromine is found naturally in cacao beans (*Theobroma cacao*) at a concentration of from about 1.5% to about 3%, and in the husk of the bean at a concentration of from about 0.7% to about 1.2%, or about 15 to about 30 g/Kg (Winholdz, 1983). Though part of the same chemical family, one must distinguish the stimulant effects of theobromine from those of caffeine. Caffeine acts relatively quickly, and its main effect on humans is increased mental alertness; theobromine's effect is subtler, and causes a mood elevation that is milder longer-lasting than that of caffeine. Theobromine's plasma half-life ($t_{1/2}$) in the bloodstream is six hours, while caffeine's is only two hours. Another difference is that theobromine is not physiologically addictive, producing no withdrawal symptoms after prolonged regular consumption, while caffeine has been proven to be physiologically addictive and linked with many cases of proven withdrawal.

Two independent studies conducted in the 1980's found that the average level of theobromine in eight varieties of commercial cocoa powder was 1.89% (Shively & Tarka, 1984 and Zoumas et al., 1980). Of particular relevance are the normal levels of theobromine found in commercially-available foodstuffs, shown below in TABLE 1.

TABLE 1

| Food Type | Theobromine Content |
|---|---|
| hot chocolate beverages | 65 mg/5-oz serving |
| chocolate milk (from instant or sweetened | 58 mg/serving |

TABLE 1-continued

| Food Type | Theobromine Content |
|---|---|
| cocoa powder) | |
| hot cocoa (average of 9 commercial mixes) | 62 mg/serving |
| cocoa cereals* | 0.695 mg/g |
| chocolate bakery products* | 1.47 mg/g |
| chocolate toppings* | 1.95 mg/g |
| cocoa beverages* | 2.66 mg/g |
| chocolate ice cream* | 0.621 mg/g |
| chocolate milk* | 0.226 mg/g |
| chocolate pudding* | 74.8 mg/serving |
| carob products* | 0-0.504 mg/g |

Sources: Zoumas, et al., 1980; Blauch & Tarka, 1983; Shivley & Tarka, 1984; Craig & Nguyen, 1984.
*Theobromine content determined by HPLC/reverse-phase column chromatography Dark chocolate contains the highest levels of theobromine per serving of any type of chocolate, but the concentrations tends to vary between about 0.36% and about 0.63%. To put this into perspective with the foodstuffs mentioned in TABLE 1, a one-ounce bar of dark chocolate contains about 130 mg of theobromine, while a one ounce bar of milk chocolate contains about 44 mg of theobromine. Thus, the concentration of theobromine in a one-ounce bar of dark chocolate is approximately two times the amount in a 5-ounce cup of hot chocolate. For a 143-pound human being to achieve a toxic level of theobromine in their blood, they would have to ingest approximately 86 one-ounce milk chocolate bars in one sitting.

Theobromine can also be isolated or produced as an amine salt (e.g., the ethylene diamine salt thereof) or a double salt thereof (e.g., with alkali metal salts or alkaline earth metal salts of organic acids, for example alkali or alkaline earth metal salts of acetic, gluconic, benzoic, or salicylic acid). The double salts may be prepared either to make the theobromine more water souble, or to make insoluble complexes.

In 1966, Strålfors reported a reduction of dental caries in hamsters that were fed diets rich in chocolate. The Strålfors study examined the effect on hamster caries by comparing cocoa powder, defatted cocoa powder, and cocoa fat. Pure cocoa powder inhibited dental caries by 84%, 75%, 60%, and 42% when the cocoa powder comprised 20%, 10%, 5%, and 2% percent of the hamster diet, respectively. Defatted cocoa showed a significantly higher anti-caries effect than did fat-containing cocoa powder, but cocoa butter alone (comprising 15% of the hamster's diet) increased dental caries significantly (Strålfors A. "Effect on Hamster Caries by Dialyzed, Detanned or Carbon-treated Water-Extract of Cocoa" Arch Oral Biol. 1966; 11:609-15.

In a follow up study, Strålfors studied the nonfat portions of the cocoa powder and demonstrated that cocoa powder washed with water possessed considerably less anti-cariogenic effect than unwashed cocoa powder. Nevertheless, Strålfors still observed a considerable anti-caries effect in the washed cocoa powder group, "indicating an existence of a non-water soluble cariostatic factor," and alluded to the existence of "two caries-inhibitory substances in cocoa: one water-soluble, and another which is sparingly soluble in water" (Strålfors, A., 1966).

Subsequent studies suggested that apatite crystals grown in vitro in the presence of theobromine were significantly larger than those grown in the absence of theobromine (see, e.g., U.S. Pat. Nos. 5,919,426 and 6,183,711, each of which is incorporated by reference in its entirety). Ingestion of theobromine by lactating rats was correlated with increased hydroxylapatite crystallite size (higher crystallinity) in the whole first molars of nursing pups exposed to theobromine, versus controls, as well as increased resistance to acid dissolution (see id.). The femurs of nursing female pups exposed to theobromine demonstrated higher crystallinity, and were stronger and stiffer than gender-matched controls; the femurs of male pups, however, did not show this relationship (see id.).

The Hall-Petch relationship, however, dictates that the resistance of a solid material to permanent deformation (e.g., its indentation hardness) increases as the particle size decreases. Consequently, the increased hydroxylapatite crystallinity observed after exposure to theobromine—coupled with the Hall-Petch relationship—suggests that the resistance of bone and teeth to indentation and permanent deformation should decrease after exposure to theobromine due to the larger crystal size. This suggestion finds support in recent work, demonstrating that "the hardness of [hydroxylapatite] follows the Hall-Petch relationship as the grain size decreases from sub-micrometers to nanometers" (Wang J. et al. "Nanocrystalline hydroxyapatite with simultaneous enhancements in hardness and toughness" Biomaterials. 2009; 30:6565-72). Another study suggests that the "hardness" of hydroxylapatite has little to do with particle size, showing almost no change in hardness with decreasing grain size, yet demonstrates that the "fracture toughness" of hydroxylapatite is increased with decreasing particle size (Mazaheri M, et al. "Effect of a novel sintering process on mechanical properties of hydroxyapatite ceramics." J. Alloys Compd. 2009; 471:180-4). A study of human adult and primary (baby) teeth demonstrated that, "[w]hen compared to the adult tooth, the baby enamel was thinner, softer, more prone to fracture, and possessed larger [hydroxylapatite] grains" (Low I M, et al "Mapping the structure, composition and mechanical properties of human teeth." Mater Sci Eng C Mater Biol App. 2008; 28:243-47.).

Because of such conflicting and paradoxical results, one cannot extrapolate the known characteristics and responses of hydroxylapatite to environmental factors to predict a reliable or accurate result cannot be predicted simply by evaluating the prior art and extrapolating a result.

BRIEF SUMMARY

In one embodiment, the present disclosure provides a composition, the composition comprising isolated theobromine, at least one source of calcium, at least one source of phosphate, and a pH of about 6.0 to about 8.5. The at least one source of calcium may be selected from the group consisting of calcium chloride, calcium carbonate, calcium gluconate, calcium phosphate, and combinations thereof. The at least one source of phosphate may be selected from the group consisting of potassium dihydrogen phosphate, dipotassium hydrogen phosphate, tripotassium phosphate, sodium dihydrogen phosphate, disodium hydrogen phosphate, trisodium phosphate, and combinations thereof. The composition may further comprise at least one isotonic agent. The isotonic agent may be a polyhydric alcohol. The polyhydric alcohol may be selected from the group consisting of xylitol, sorbitol, mannitol, maltitol, lactitol, isomalt, erythritol, arabitol, glycerol, and combinations thereof. The composition may further comprise at least one thickener. The thickener may be selected from the group consisting of methyl cellulose, carboxymethyl cellulose, ethyl cellulose, hydroxypropyl cellulose, hydroxypropyl methylcellulose, and combinations thereof. The composition may further comprise an antibacterial agent. The antibacterial agent may be triclosan, hydrogen peroxide ($H_2O_2$), methyl-4-hydroxybenzoate, clove oil, benzalkonium chloride, or combinations thereof.

In one aspect of this embodiment, a composition is provided for enhancing the hardness of at least one tooth, wherein said composition enhances said hardness more than a dentifrice containing 0% to about 1.1% of either sodium fluoride or sodium monofluorophosphate. In a related aspect, the composition enhances said hardness more than a dentifrice containing 0% to about 0.5% of sodium fluoride or 0% to about 0.76% sodium monofluorophosphate. In a related aspect, the composition enhances said hardness more than a dentifrice containing 0% to about 0.25% of sodium fluoride or 0% to about 0.76% sodium monofluorophosphate. In a related aspect, the composition enhances said hardness more than a dentifrice containing 0% to about 0.15% of sodium fluoride or 0% to about 0.76% sodium monofluorophosphate.

In one embodiment, the present disclosure provides a method of treating dental surfaces in a mammal in need thereof, said method comprising: providing a composition comprising isolated theobromine, theobromine salt, or theobromine double salt, at least one source of calcium, and at least one source of phosphate, wherein the pH of said composition is about 6.0 to about 8.5; and administering said composition to said mammal. The least one source of calcium may be selected from the group consisting of calcium chloride, calcium carbonate, calcium gluconate, calcium phosphate, and combinations thereof. The at least one source of phosphate may be selected from the group consisting of potassium dihydrogen phosphate, dipotassium hydrogen phosphate, tripotassium phosphate, sodium dihydrogen phosphate, disodium hydrogen phosphate, trisodium phosphate, and combinations thereof. The composition of said method may further comprise at least one isotonic agent. The isotonic agent may be a polyhydric alcohol. The polyhydric alcohol may be selected from the group consisting of xylitol, sorbitol, mannitol, maltitol, lactitol, isomalt, erythritol, arabitol, glycerol, and combinations thereof. The composition of said method may further comprise at least one thickener. The thickener may be selected from the group consisting of methyl cellulose, carboxymethyl cellulose, ethyl cellulose, hydroxypropyl cellulose, and combinations thereof. The composition may further comprise an antibacterial agent, an antimicrobial agent, or combinations thereof. The antibacterial agent may be selected from the group consisting of triclosan, hydrogen peroxide, methyl-4-hydroxybenzoate, clove oil, and combinations thereof.

In one aspect of this embodiment, a composition is provided for treating a dental surface of at least one tooth, wherein said composition treats said dental surface better than a dentifrice containing 0% to about 1.1% of either sodium fluoride or sodium monofluorophosphate. In one aspect of said method, the composition treats said dental surface better than a dentifrice containing 0% to about 0.5% of sodium fluoride or 0% to about 0.76% sodium monofluorophosphate. In one aspect of said method, the composition treats said dental surface better than a dentifrice containing 0% to about 0.25% of sodium fluoride or 0% to about 0.76% sodium monofluorophosphate. In one aspect of said method, the composition treats said dental surface better than a dentifrice containing 0% to about 0.15% of sodium fluoride or 0% to about 0.76% sodium monofluorophosphate. In one aspect, said dental surface is scratched, chipped, eroded, abraded, pitted, damaged by dental caries, and/or damaged by other trauma.

In one embodiment, the present disclosure provides a method of enhancing the indentation hardness of at least one tooth, said method comprising providing a composition comprising isolated theobromine, theobromine salt, or theobromine double salt, at least one source of calcium, and at least one source of phosphate, wherein the pH of said composition is about 6.0 to about 8.5; and administering said composition to said mammal. The at least one source of calcium may be selected from the group consisting of calcium chloride, calcium carbonate, calcium gluconate, calcium phosphate, and combinations thereof. The at least one source of phosphate may be selected from the group consisting of potassium dihydrogen phosphate, dipotassium hydrogen phosphate, tripotassium phosphate, sodium dihydrogen phosphate, disodium hydrogen phosphate, trisodium phosphate, and combinations thereof. The composition of said method may further comprise at least one isotonic agent. The isotonic agent may be a polyhydric alcohol. The polyhydric alcohol may be selected from the group consisting of xylitol, sorbitol, mannitol, maltitol, lactitol, isomalt, erythritol, arabitol, glycerol, and combinations thereof. The composition of said method may further comprise at least one thickener. The thickener may be selected from the group consisting of methyl cellulose, carboxymethyl cellulose, ethyl cellulose, hydroxypropyl cellulose, and combinations thereof. The composition of said method may further comprise an antibacterial agent, an antimicrobial agent, or combinations thereof. The antibacterial agent may be selected from the group consisting of triclosan, hydrogen peroxide, methyl-4-hydroxybenzoate, clove oil, and combinations thereof. The enhancing may further comprise deposition of new hydroxylapatite and/or calcium phosphate onto said tooth.

In one aspect of this embodiment, a composition is provided for enhancing the indentation hardness of at least one tooth, wherein said composition enhances said indentation hardness more than a dentifrice containing 0% to about 1.1% of either sodium fluoride or sodium monofluorophosphate. In one aspect of said method, the composition enhances said indentation hardness more than a dentifrice containing 0% to about 0.5% of sodium fluoride or 0% to about 0.76% sodium monofluorophosphate. In one aspect of said method, the composition enhances said indentation hardness more than a dentifrice containing 0% to about 0.25% of sodium fluoride or 0% to about 0.76% sodium monofluorophosphate. In one aspect of said method, the composition enhances said indentation hardness more than a dentifrice containing 0% to about 0.15% of sodium fluoride or 0% to about 0.76% sodium monofluorophosphate.

BRIEF DESCRIPTION OF THE DRAWINGS

For a further understanding of the nature, objects, and advantages disclosed by the present application, reference should be had to the following detailed description, read in conjunction with the following drawings, wherein like reference numerals denote like elements.

FIG. 12A shows such a tooth incubated in control solution (artificial saliva); FIG. 12B shows such a tooth incubated in a solution containing 0.25% NaF; and FIG. 12C shows such a tooth incubated in a solution containing 200 mg/L theobromine.

DETAILED DESCRIPTION

Figure 1:
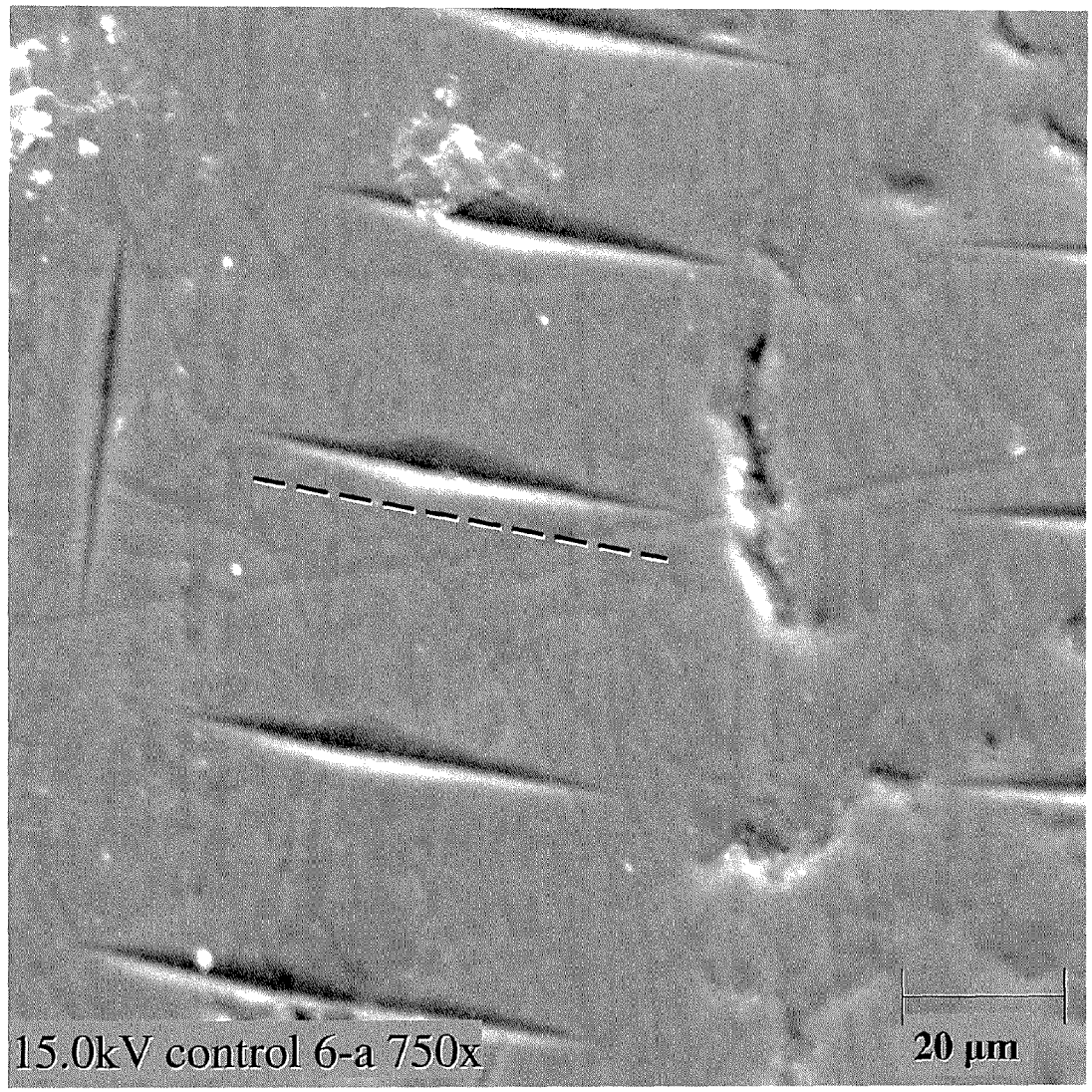
FIG. 1 shows indentations in tooth enamel following microhardness testing. The dashed line indicates the length (L) of the long diagonal, used in calculating the Knoop hardness number (HK).
Figure 2:
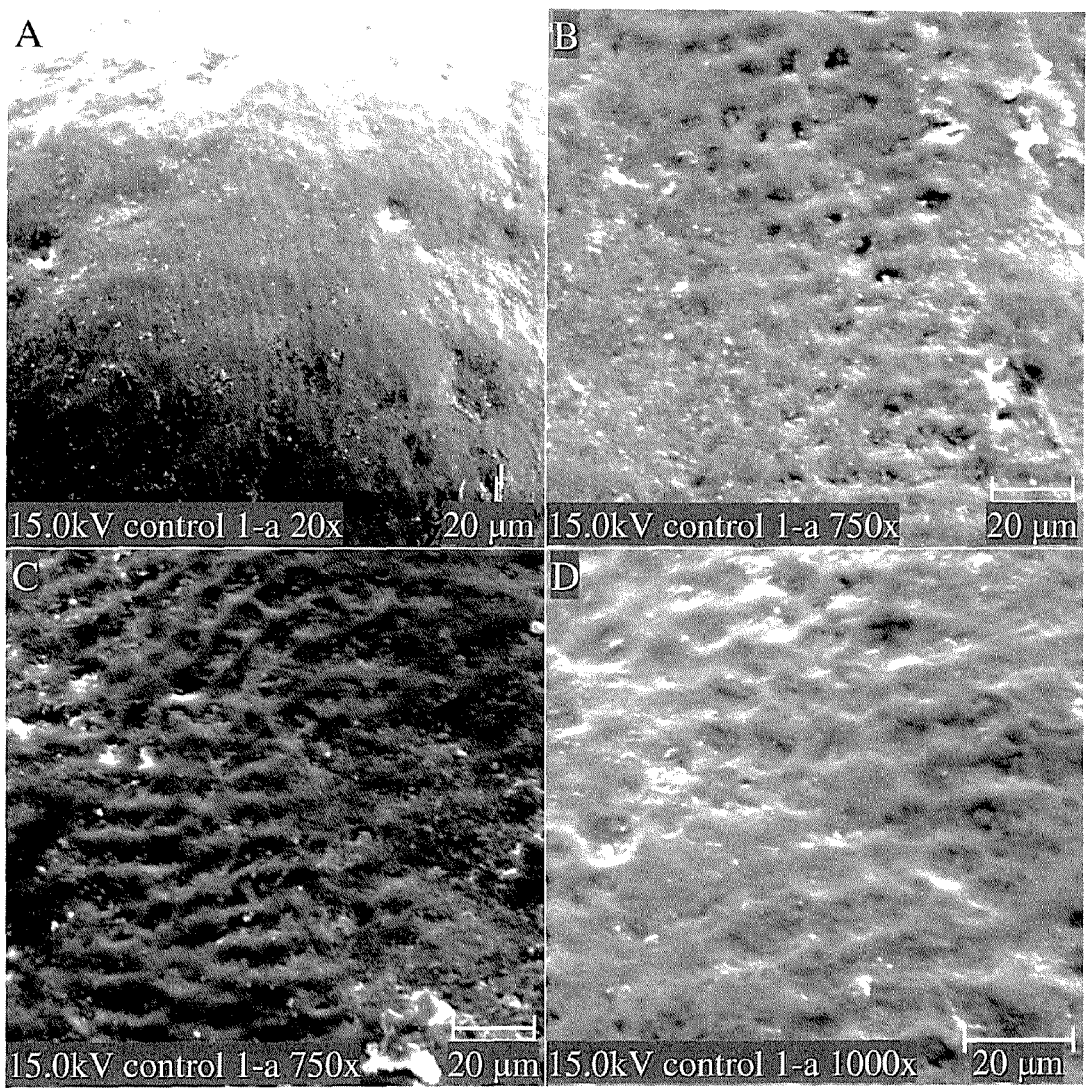
FIG. 2 shows scanning electron micrographs of a control tooth at different magnifications.
Figure 3:
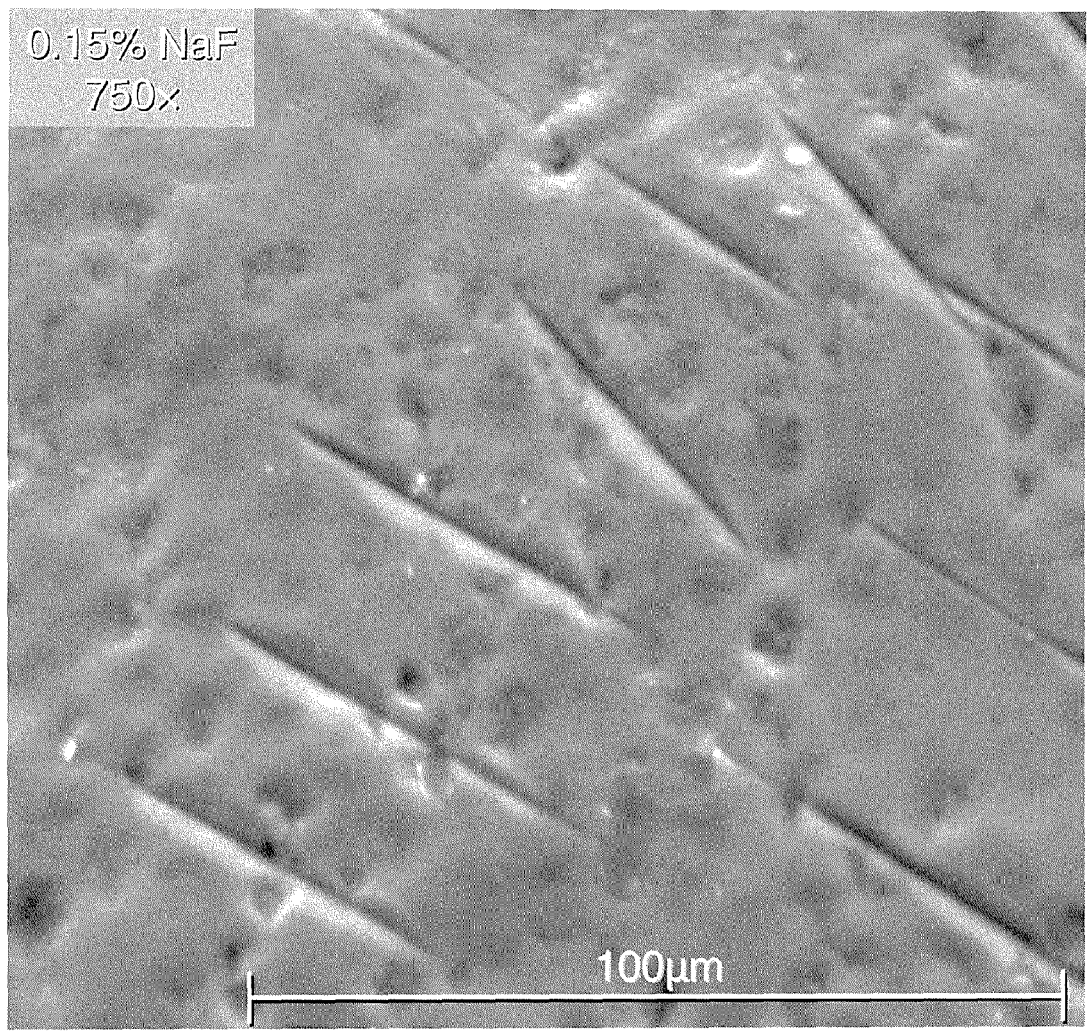
FIG. 3 shows indentations in tooth enamel of a tooth exposed to 0.15% NaF (750× mag.).
Figure 4:
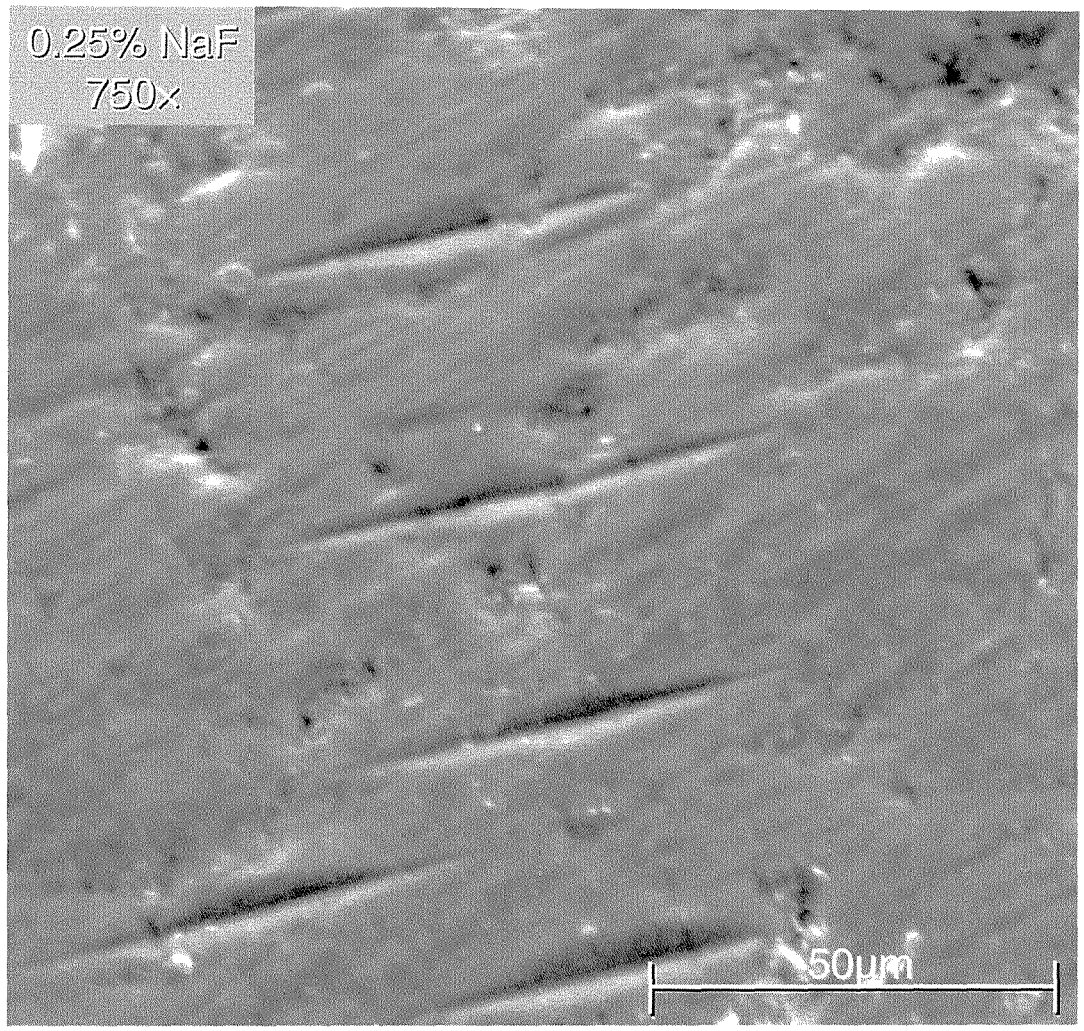
FIG. 4 shows indentations in tooth enamel of a tooth exposed to 0.25% NaF (750× mag.).
Figure 5:
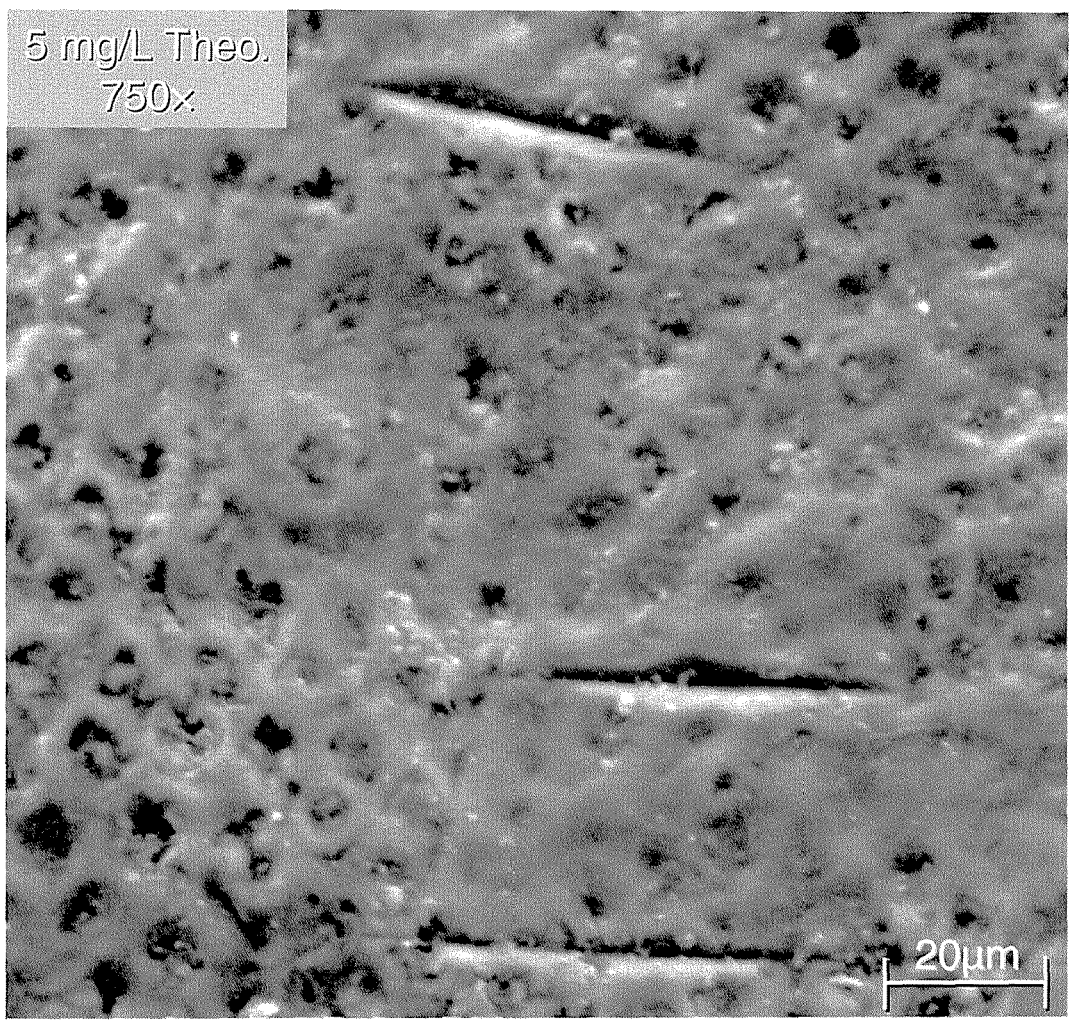
FIG. 5 shows indentations in tooth enamel of a tooth exposed to 5 mg/L theobromine (750× mag.).
Figure 6:
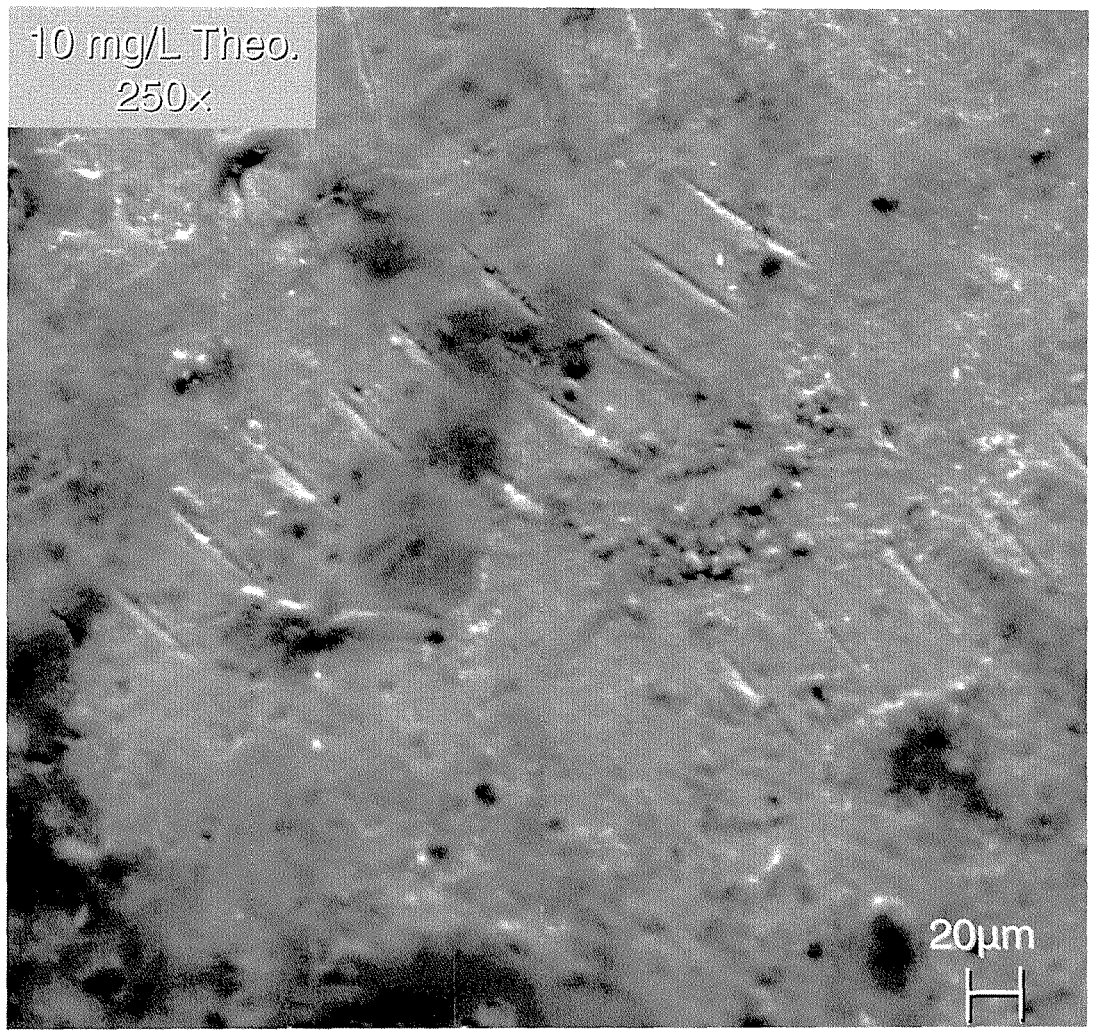
FIG. 6 shows indentations in tooth enamel of a tooth exposed to 10 mg/L theobromine (250× mag.).
Figure 7:
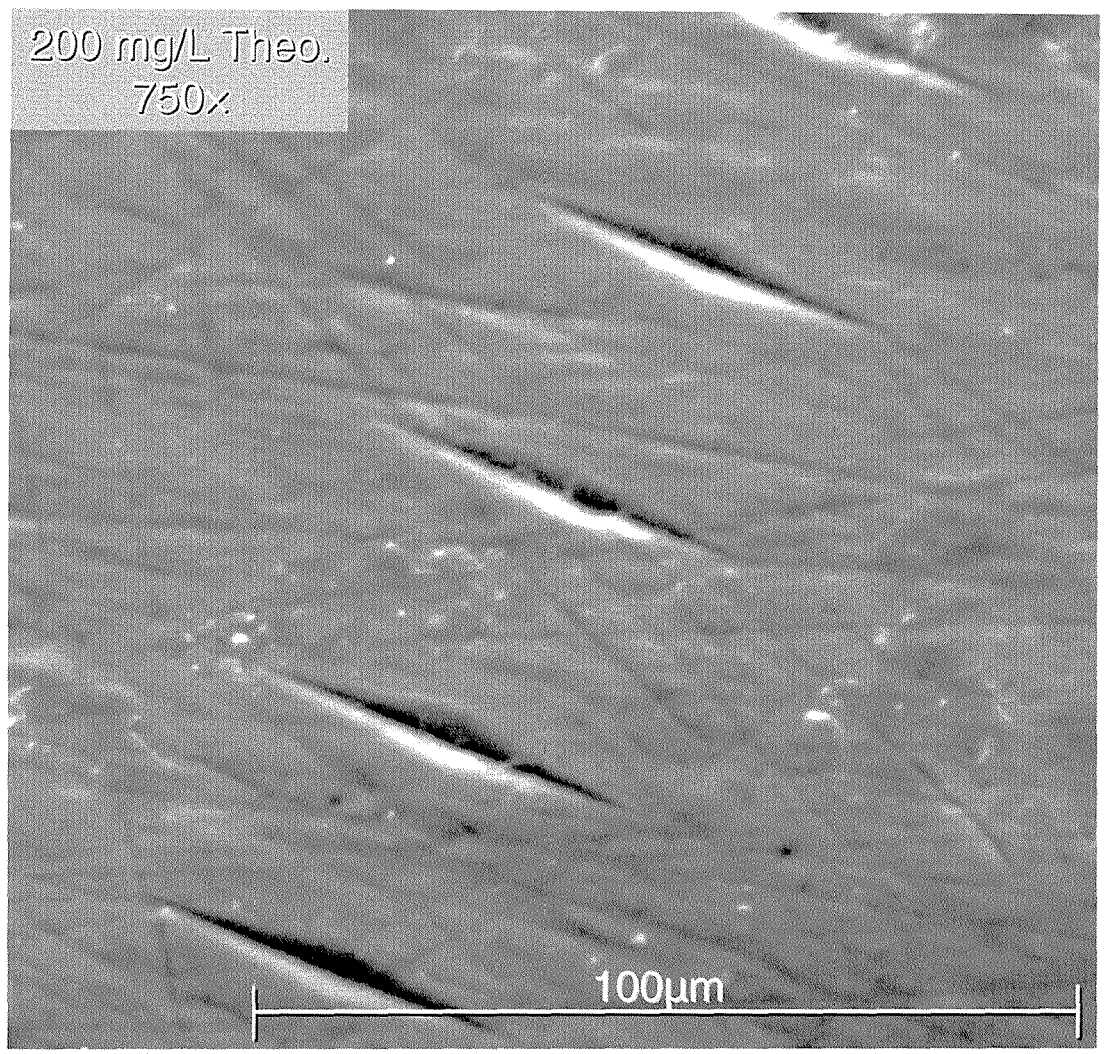
FIG. 7 shows indentations in tooth enamel of a tooth exposed to 200 mg/L theobromine (750× mag.).
Figure 8:
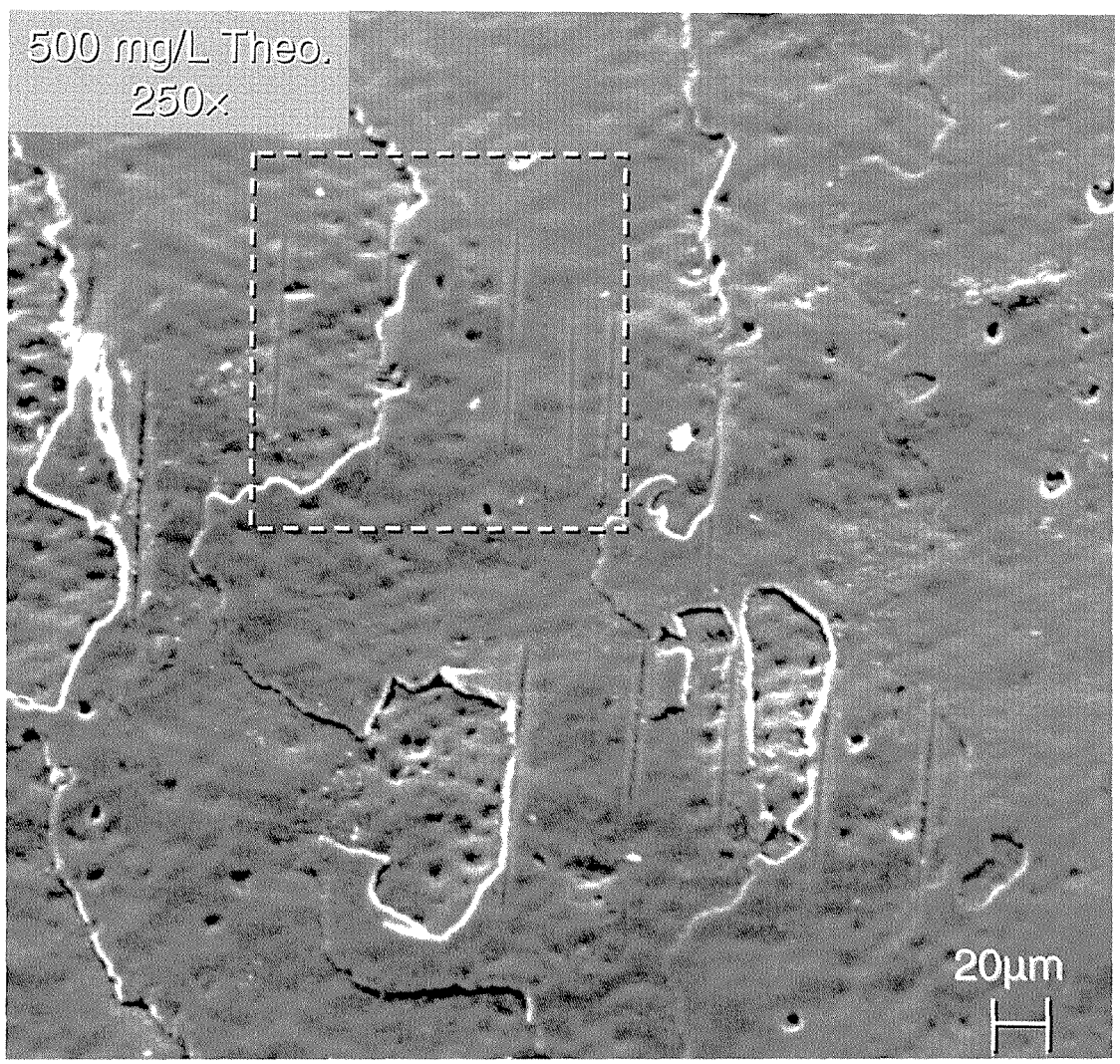
FIG. 8 shows indentations in tooth enamel of a tooth exposed to 500 mg/L theobromine (250× mag.). The dashed box within FIG. 8 indicates the area shown in FIG. 9 at 750× magnification.
Figure 9:
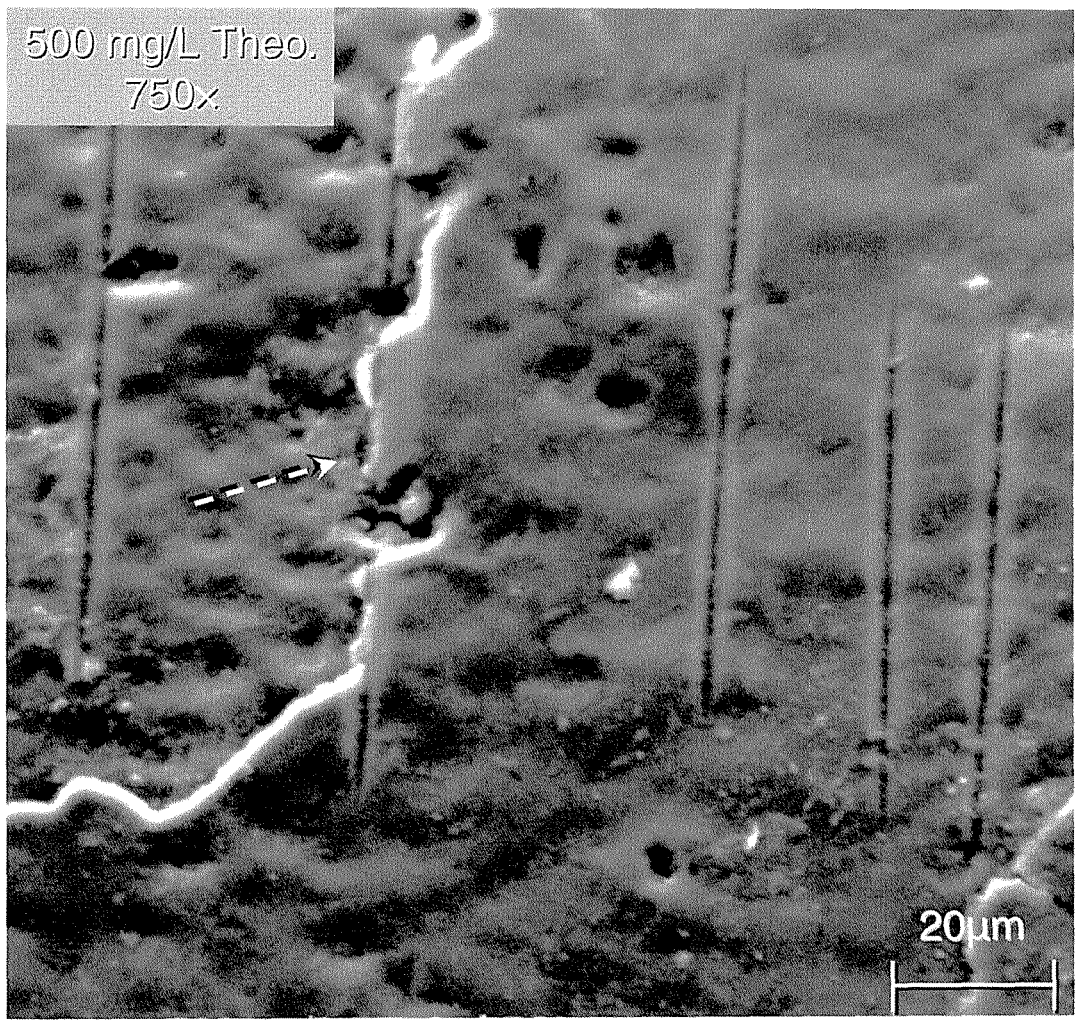
FIG. 9 shows the area bounded by the dashed square in FIG. 8, and shows indentations in tooth enamel of a tooth exposed to 500 mg/L theobromine (750× mag.).

Before the subject of the instant application is further described, it is to be understood that the instant application is not limited to the particular embodiments described below, as variations of the particular embodiments may be made and still fall within the scope of the appended claims. It is also to be understood that the terminology employed is for the purpose of describing particular embodiments, and is not intended to be limiting. Instead, the scope of the instant application will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which the subject of the instant application belongs.

The present disclosure comprises a theobromine composition, useful for enhancing the mechanical resistance of teeth, as well as a method of enhancing the mechanical resistance of teeth, the method comprising administering the theobromine composition of the present disclosure to a mammal in need thereof.

The theobromine of the instant composition and method may be isolated or produced as an amine salt (e.g., the ethylene diamine salt thereof) or a double salt thereof (e.g., with alkali metal salts or alkaline earth metal salts of organic acids, for example alkali or alkaline earth metal salts of acetic, gluconic, benzoic, or salicylic acid). The double salts may be prepared either to make the theobromine more water souble, or to make insoluble complexes. Suitable acid addition salts of theobromine include the acid addition salts including pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methanesulphonate, a-keto glutarate, a-glycerophosphate and glucose-1-phosphate. Preferably, the acid addition salt is a hydrochloride salt. The chemistry, physical properties, production, use, occurrence, metabolism, toxicity, analysis and carcinogenicity of methylxanthines were reviewed by a working group of the International Agency for Research on Cancer (World Health Organization, Coffee, tea, mate, methylxanthines and methylglyoxal, IARC Monograph on the Evaluation of Carcinogenic Risks to Humans, Vol. 51 (1991).

The compounds of the theobromine composition are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90%, and still more preferably 95%.

The theobromine concentration may be from about 0.1 to about 1000, from about 0.25 to about 900, from about 0.5 to about 800, from about 0.5 to about 700, from about 0.75 to about 600, from about 1 to about 500, from about 5 to about 500, from about 10 to about 450, from about 25 to about 400, from about 50 to about 350, from about 100 to about 300, from about 150 to about 250, from about 175 to about 225, and preferably about 200 mg/L.

Accordingly, the present disclosure provides a theobromine composition comprising isolated theobromine, or a salt or double salt thereof, at least one source of calcium, and at least one source of phosphate, where the pH of the composition is from about 5 to about 10, from about 5.5 to about 9.5, from about 6.0 to about 9.0, from about 6.0 to about 8.5, from about 6.5 to about 8.5, from about 6.8 to about 8.2, from about 7.0 to about 8.0, from about 7.2 to about 7.8, and preferably from about 7.4 to about 7.6.

The theobromine composition is formulated for oral or topical oral administration, and may be formulated for slow or rapid release of the active ingredients. For example, the theobromine composition may be in the form of tablets (including orally-disintegrating tablets), gums (e.g., chewing gum), sachets, powders, granules, lozenges, reconstitutable powders, and liquid, gel, or paste preparations such as oral solutions or suspensions. Topical oral formulations are also envisioned, where appropriate (e.g., toothpaste, mouthwash, dental floss, over-the-counter trays, coated strips, orthodontic and pediatric varnishes, dental cements or adhesives, polishing pastes, tooth bleaching agents, and cavity filling materials and resins (both UV reactive and non-UV reactive)), as well as the incorporation of the theobromine composition into foodstuffs (e.g., baked goods, beverages, etc.) and endodontic materials (e.g., gutta percha, etc. containing the theobromine composition), all of which may be used with or without prior acid etching of a dental surface (see, e.g., EXAMPLE 4 below). To obtain consistency of administration it is preferred, but not necessary, that the composition is provided as a unit dose.

The formulations may contain conventional excipients such as binding agents (e.g., syrups such as corn syrup, acacia, gelatin, sorbitol, tragacanth, polyvinylpyrrolidone, polyethylene glycols (PEG), waxes and other fats, cocoa butter, cocoa butter substitutes, hydrogenated tallow, hydrogenated vegetable oils, hydrogenated cotton seed oil, palm kernel oil, soybean oil, stannol esters, glycerol esters, polyalcohol esters, polyoxyethylene esters of hydrophilic and hydrophobic balances from 0.5 to above 20 and polyethylene glycols, monosaccharides, oligosaccharides (dextrose, dextrose monohydrate, lactose, mannose, fructose, and derivatives and mixtures thereof), polysaccharides, gum solutions, hydrogenated starch hydrolates, glycerine, and mixtures thereof; fillers (e.g., silicon dioxide, sugars, starches, lactose, sucrose, sorbitol, fructose, talc, stearic acid, magnesium stearate, dicalcium phosphate, erythitol, xylitol, mannitol, maltitol, isomalt, dextrose, maltose, lactose, microcrystalline celluloses, maize-starch, glycine, and mixtures thereof); lubricants (e.g., magnesium stearate, calcium stearate, talc, starches, silicon dioxide, and mixtures thereof); disintegrants (e.g., starch, polyvinylpyrrolidone, sodium starch glycollate, microcrystalline cellulose, and mixtures thereof); bonding agents (e.g., polyethylene glycols in solid form, monoglycerides (40-90% glycerides of vegetable or animal fats), acetylated monoglycerides, hydrocolloidal gums, other emulsifiers or fats and mixtures thereof); or pharmaceutically acceptable wetting agents (e.g., sodium lauryl sulphate).

Solid, orally-disintegrable, or chewable oral compositions may be prepared by conventional methods of blending, filling, tabletting, soaking, or the like, and may be in the form of for example, tablets (including orally-disintegrating tablets), gums, sachets, powders, granules, lozenges, reconstitutable powders, liquid, gel, or paste preparations such as oral solutions or suspensions, and foodstuffs such as mints, gums, candies, and baked goods. Repeated blending operations may be used to distribute the active agent throughout those compositions employing large quantities of fillers. The chewable or orally-disintegrable compositions may be produced, inter alia, by subjecting a feedstock containing a carrier material to flashflow processing, thereby producing a shearform matrix, or "floss", as taught by the prior art. The shearform matrix can then be mixed by conventional techniques with active ingredients (e.g., isolated theobromine, a source of calcium, a source of phosphate). Gutta percha, the predominant material used to obturate the space inside of a tooth after endodontic therapy (e.g., after a root canal), may be impregnated (e.g., by immersion) with a theobromine composition of the instant disclosure.

Liquid oral preparations may be in the form of for example, emulsions, syrups, mouthwashes (rinses), or elixirs, or may be presented as a dry product for reconstitution with water or other suitable vehicle before use (e.g., as a sports drink). Such liquid preparations may contain conventional additives such as suspending agents, for example sorbitol, syrup, methyl cellulose, gelatin, hydroxyethylcellulose, carboxymethylcellulose, aluminum stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Topical oral formulations may be presented as, for instance, ointments, creams, lotions, impregnated dressings, gels, gel sticks, sprays, and aerosols, and may contain appropriate conventional additives such as preservatives and/or solvents to assist drug penetration and emollients in ointments and creams. The formulations may contain compatible conventional carriers, such as cream or ointment bases and ethanol or oleyl alcohol for lotions.

The theobromine compositions and formulations may contain from about 0.01% to about 0.1%, to about 1.0%, to about 2.5%, to about 5%, to about 10%, to about 20%, to about 50%, or to about 99% by weight, preferably from about 0.01% to about 0.1%, to about 1.0%, to about 2.5%, to about 5%, to about 10%, to about 20%, or to about 50% by weight, and more preferably from about 0.1% to about 0.1%, to about 1.0%, to about 2.5%, to about 5%, to about 10%, to about 20%, to about 50% of isolated theobromine, depending on the formulation.

It is important to note that the resistance of a solid material to deformation depends upon its microdurability (small-scale shear modulus) in any direction, and not upon any rigidity or stiffness properties such as its bulk modulus or Young's modulus. Observers often confuse stiffness and hardness. For example, reports occasionally describe materials as being harder than diamond, but fail to account for the anisotropy of the materials' solid cells (the different values of measured properties, when measured in different directions). This failure accounts for the reported materials' propensity for spalling and flaking in squamose or acicular habits in other dimensions (e.g., osmium is stiffer than diamond, but only as hard as quartz).

The Hall-Petch relationship describes the relationship between a solid material's particle size and its resistance to permanent deformation (e.g., its indentation hardness), and predicts that yield strength increases as the particle size decreases. The relationship is based upon the observation that grain boundaries—the interfaces between grains in a polycrystalline material—disrupt the motion of dislocations through a material and that the number of dislocations within a grain affects the ease with which dislocations traverse grain boundaries and travel from grain to grain. Thus, modifying grain size (e.g., via heat treatment, or by altering the rate of solidification) may influence dislocation movement and yield strength. With particle sizes smaller than about 10 nm, however, the yield strength either remains constant or decreases with decreasing particle size.

Prior studies indicated that apatite crystals grown in vitro demonstrate enhanced crystallinity (increased grain size) when grown in the presence of theobromine. The in vitro result is mirrored by results from experiments in which lactating female rats were fed theobromine and the hydroxylapatite crystallinity of teeth and femurs from nursing pups was measured. The femurs of female pups showed increased yield stress, but the femurs of male pups showed decreased yield stress. Thus, the increased grain size observed after theobromine exposure suggest reduced yield strength, especially in view of work by Wang et al, demonstrating that "the hardness of [hydroxylapatite] follows the Hall-Petch relationship as the grain size decreases from sub-micrometers to nanometers." The increased yield strength in the femurs of female rats but not those of male rats suggests—for bones—the possible involvement of a confounding factor (e.g., a factor that ameliorated reduced yield strength, in the face of increased grain size, in females but not males).

Without wishing to be bound by theory, applicant believes that etching the dental surface enhances the deposition of new calcium phosphate and/or hydroxylapatite. A one-step etching process may be employed using any inorganic acid including, but not limited to, HCl (hydrochloric acid), $HNO_3$ (nitric acid), $H_2SO_4$ (sulfuric acid), and/or $H_3PO_4$ (phosphoric acid), and/or any organic acid including, but not limited to, lactic acid, pyruvic acid, glycolic acid, chloroacetic acid, dichioroacetic acid, trichioroacetic acid, cyanoacetic acid, tartaric acid, succinic acid, glutaric acid, maleic acid, fumaric acid, malonic acid, citraconic acid, ortho-phthalic acid, meta-phthalic acid, para-phthalic acid, citric acid, tricarballyic acid, 1,3,5-pentanetricarboxylic acid, trimellitic acid, 2-acrylamido-2-methyipropane sulfonic acid, benzenesulfonic acid, benzoic acid, bromoacetic acid, 10-camphorquinonesulfonic acid, 10-camphorsulfonic acid, dibromoacetic acid, 2,4-dinitrophenol, formic acid, fumaric acid, 2-hydroxy-4-methoxybenzophenone-5-sulfonic acid, maleic-acid, 2-naphthalene sulfonic acid, nitric acid, oxalic acid, p-nitrophenol, phenol, phosphorous acid esters (such as 2,2'-bis(a-methacryloxy-b-hydroxypropoxyphenyl)propane diphosphonate (Bis-GMA diphosphonate), dibutyl phosphite, di-2-ethyl-hexyl phosphate, di-2-ethyl-hexyl phosphite, hydroxyethyl methacrylate monophosphate, glyceryl dimethacrylate phosphate, glyceryl-2-phosphate, glyceryiphosphoric acid, methacryloxyethyl phosphate, pentaerythritol triacrylate monophosphate, pentaerythritol trimethacrylate monophosphate, dipentaerythritol pentaacrylate monophosphate, and dipentaerythritol pentamethacrylate monophosphate), toluene sulfonic acid, tribromoacetic acid, trifluoroacetic acid, trifluoromethanesulfonic acid, and/or trihydroxybenzoic acid), and mixtures thereof. A two-step etching process may also be used, as described at EXAMPLE 4, using any of the aforementioned acids. The concentration of said acid or acids may be (independently) from about 0.01 M to about 2 M, from about 0.025 M to about 1.5 M, from about 0.05 M to about 1 M, from about 0.075 M to about 0.75 M, from about 0.085 M to about 0.5 M, from about 0.09 M to about 0.4 M, from about 0.1 M to about 0.3 M, from about 0.1 M to about 0.25 M, from about 0.1 M to about 0.2 M, and preferably about 0.1 M. Preferably, a two-step etching process is employed comprising irrigation/immersion/exposure for about 15 seconds in/to 0.1 M HCl, rinse with distilled water, then irrigation/immersion/exposure for about 15 seconds to a 0.1 M oxalic acid solution, and then rinse once more with distilled water.

Here, the applicants present the unexpected and surprising result that human teeth exposed to a theobromine composition demonstrate significantly enhanced indentation hardness despite concomitant increase in grain size. Applicants also present the further unexpected and surprising result that such exposure produces significant deposition of new hydroxylapatite/calcium phosphate onto dental surfaces, and that such deposition is to a greater degree than that observed in either control situations or with NaF. This discovery represents a significant advance in the prevention of dental injuries including tooth fractures (generally), fractures of the enamel, chipping, and caries.

Example 1

Testing Fluoride vs. Theobromine

Using a Buehler isomet low-speed saw equipped with a series 15HC diamond blade, thirteen human teeth were each cut into four approximately equal sections, thus providing thirteen groups containing four samples in each group. The backside (the cut surface) of each sample was ground flat and affixed to a bronze compression cap with an adhesive, leaving the original outer surface of the tooth exposed and available for experimentation. One sample from each group (i.e., one sample from each tooth) was used for each of three experimental conditions, reserving one sample per group (i.e., reserving one sample per tooth) in the event that flat areas suitable for microhardness testing were not available.

Samples were immersed in either control solution (artificial saliva, as shown in TABLE 2), control solution containing NaF, or control solution containing theobromine, for thirty minutes daily. Following this daily immersion regimen, samples were rinsed with distilled water and placed in control solution (artificial saliva) for the remainder of the 24-hour period. The only exception to this rinsing regimen occurred on the eighth day, when the rinsing step was omitted in order to avoid disrupting the enamel surfaces prior to subjecting the samples to scanning electron microscopy (SEM).

TABLE 2

| Reagent | Amount | Preferred Amount |
|---|---|---|
| Carboxymethylcellulose | 0-9.0 g | 9.0 g |
| KCl | 0-1.2 g | 1.2 g |
| NaCl | 0-0.84 g | 0.84 g |
| $MgCl_2 \cdot 6H_2O$ | 0-0.06 g | 0.06 g |
| $MgCl_2$ | 0-0.0281 g | 0.0281 g |
| $CaCl_2 \cdot 2H_2O$ | 0.1-1.0 g | 0.32 g |
| $K_2HPO_4$ | 0.1-1.0 g | 0.34 g |
| Sorbitol Solution (70%, aqueous) | 0-50 g | 42.80 g |
| Xylitol | 0-3.0 g | 3.0 g |
| Oil of Lemon | 0-0.4 g | 0.4 g |
| Methyl-4-hydroxybenzoate | 0-3.0 g | 2.0 g |
| Tricloscan | 0-1.5 g | 1.5 g |
| Distilled Water | to 1000 mL | to 1000 mL |
| pH | 6-8.5 | 6-8.5 |

Sodium fluoride was examined at concentrations of 0.15% (about 35.7 mM), 0.25% (about 59.5 mM), 0.5% (about 119 mM), and 1.1% (about 262 mM), representing both the lower end of commercially-available (over-the-counter) sodium fluoride concentrations, and the prescription-strength level of 1.1%. The effects of theobromine were studied at concentrations of 1 mg/L (about 0.006 mM), 5 mg/L (about 0.028 mM), 10 mg/L (about 0.056 mM), 25 mg/L (about 0.139 mM), 50 mg/L (about 0.278 mM), 100 mg/L (about 0.556 mM), 200 mg/L (about 1.11 mM), and 500 mg/L (about 2.78 mM). A wider dose range of was used for theobromine because the effective dosage was unknown. The highest dose of theobromine—500 mg/L—corresponds to the average level of theobromine found in commercial cocoa powder (about 1.89%), as mentioned above, and represents the upper solubility limit of theobromine in water. The 500 mg/L theobromine was made by mixing 1890 mg (1.89 g) theobromine per liter of artificial saliva.

Pure hydroxylapatite has a calcium-to-phosphorus (Ca:P) ratio of 1.67 to 1. Tri-calcium phosphate $Ca_3(PO_4)_2$, or "TCP," is the major impurity found in hydroxylapatite and can be detected by x-ray diffraction as a deviation of the Ca:P ratio away from the target ratio of 1.67:1. Tri-calcium phosphate formation is easily minimized by ensuring the presence of sufficient calcium (e.g., as calcium chloride) in the artificial saliva solution (Van Der Bill and De Waal (1993), Kelly et al. (2004)). The applicants' formulation deviates from the literature in that the artificial saliva solution contains twice the usual amount of calcium chloride (0.32 g/L of $CaCl_2 \cdot 2H_2O$) so as to minimize TCP formation. The addition of an effective threshold level of calcium is also of particular concern for the development of applicants' dentifrice.

Example 2

Knoop Microhardness Testing

Knoop microhardness tests were performed on each sample, each day, for eight days, using a Buehlet Micromet-1 microhardness tester fitted with an elongated diamond-shaped indenter tip. Day one measurements represent the baseline hardness for each sample. Because each tooth was cut into four different samples, applicants were able to compare different experimental conditions on roughly the same enamel surfaces. For groups where all four sectioned specimens from one tooth had flat surfaces that were suitable for Knoop microhardness testing, additional theobromine dosages were examined, since there were more benchmark values examined in the theobromine experimental group.

The Micromet-1 diamond tip was lowered to make contact with the enamel surface of each tooth specimen. Once contact was made, the microhardness indenter applied 50 grams of force to the enamel surface of each sample, for 5 seconds. The force applied was roughly perpendicular to the enamel surface. When finished, the diamond tip retracted automatically, and the length of the long diagonal of indentation, apparent on the enamel surface of each sample, was measured via scanning electron microscopy (See, e.g., FIG. 1). Indentation lengths were used to calculate microhardness values (the Knoop hardness number, or "HK") according to Formula 1:

$$HK = \frac{\text{load}}{\text{area}} = \frac{P}{C_p L^2} \qquad \text{Formula 1}$$

where HK values typically range from 100 to 1000 Pascals (Pa, or kgf/mm$^2$; where 1 kgf/mm$^2$=9.80665 MPa); P=load (here, 50 gf); area=impression area; $C_p$=correction factor related to the shape of the indenter relating projected area of the indentation to the square of the length of the long diagonal (here, 0.07 for the diamond-shaped indenter used); and L=length of indentation, along its long axis (μm).

Example 3

Scanning Electron Micrographs

Scanning electron micrographs (SEMs) were taken using an Amray 1820 digital SEM at 15 kv acceleration voltage, and 18 mm working distance, 25° sample tilt, and a 400 μm final aperture. Multiple 512×512 pixel 24-bit tiff images were collected via EDS 2006, which is part of an integrated software package by IXRF Systems Inc. (See, e.g., FIGS. 1-9).

As explained above in EXAMPLE 2, the length of each indentation apparent on the enamel surface of each sample was measured under a microscope (See, e.g., FIGS. 1, 3-9). Indentation lengths were used to calculate microhardness values (HK) according to Formula 1. The teeth treated with theobromine composition of the present disclosure demonstrated considerable sheeting and surface recrystallization on the enamel surfaces. Teeth treated with the 500 mg/L (about 2.78 mM) theobromine composition demonstrated such tremendous surface recrystallization that the newly-deposited hydroxylapatite deposits began to cover up the original pitted and porous surfaces (see FIGS. 8 & 9). These scanning electron micrographs suggest that the theobromine composition disclosed here acts as a kind of catalyst for hydroxylapatite formation on tooth surfaces.

Figure 10:
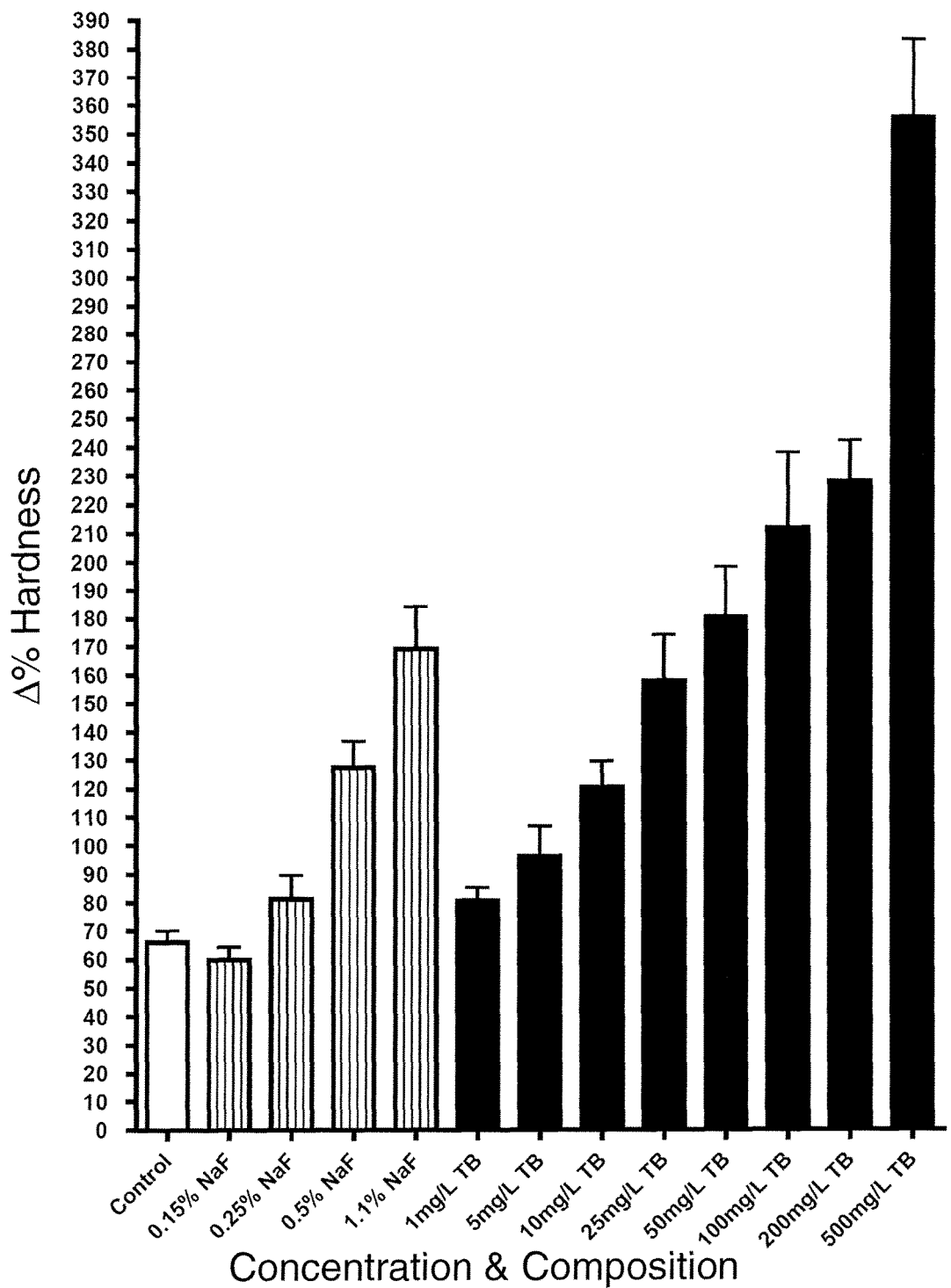
FIG. 10 is a bar graph showing the effects of different concentrations of NaF and theobromine on microhardness.

As demonstrated by the graph of FIG. 10, following exposure of teeth to the theobromine composition of the present disclosure under the conditions described in EXAMPLE 1, as little as 1 mg/L theobromine (about 0.006 mM) produced—remarkably, and unexpectedly—results equivalent to those achieved with 0.25% (w/v) sodium fluoride (about 59.5 mM), the amount of fluoride commonly found in commercial dentifrices. Because sodium monofluorophosphate (Na$_2$FPO$_3$) contains one fluoride ion per molecule (just as sodium fluoride does), the dose/response profile observed with NaF is expected to be about the same for Na$_2$FPO$_3$. As clearly demonstrated by FIG. 10, little as 25 mg/L theobromine (about 0.139 mM) produced results equivalent to those achieved with 1.1% sodium fluoride (about 262 mM), the amount found in prescription-strength toothpastes. Remarkably, between 100 mg/L and 500 mg/L theobromine produced dramatic improvements in microhardness values over the 8-day testing period. Recall that 500 mg/L theobromine corresponds to the average level of theobromine found in commercial cocoa powder (about 1.89%), as mentioned above.

Figure 11:
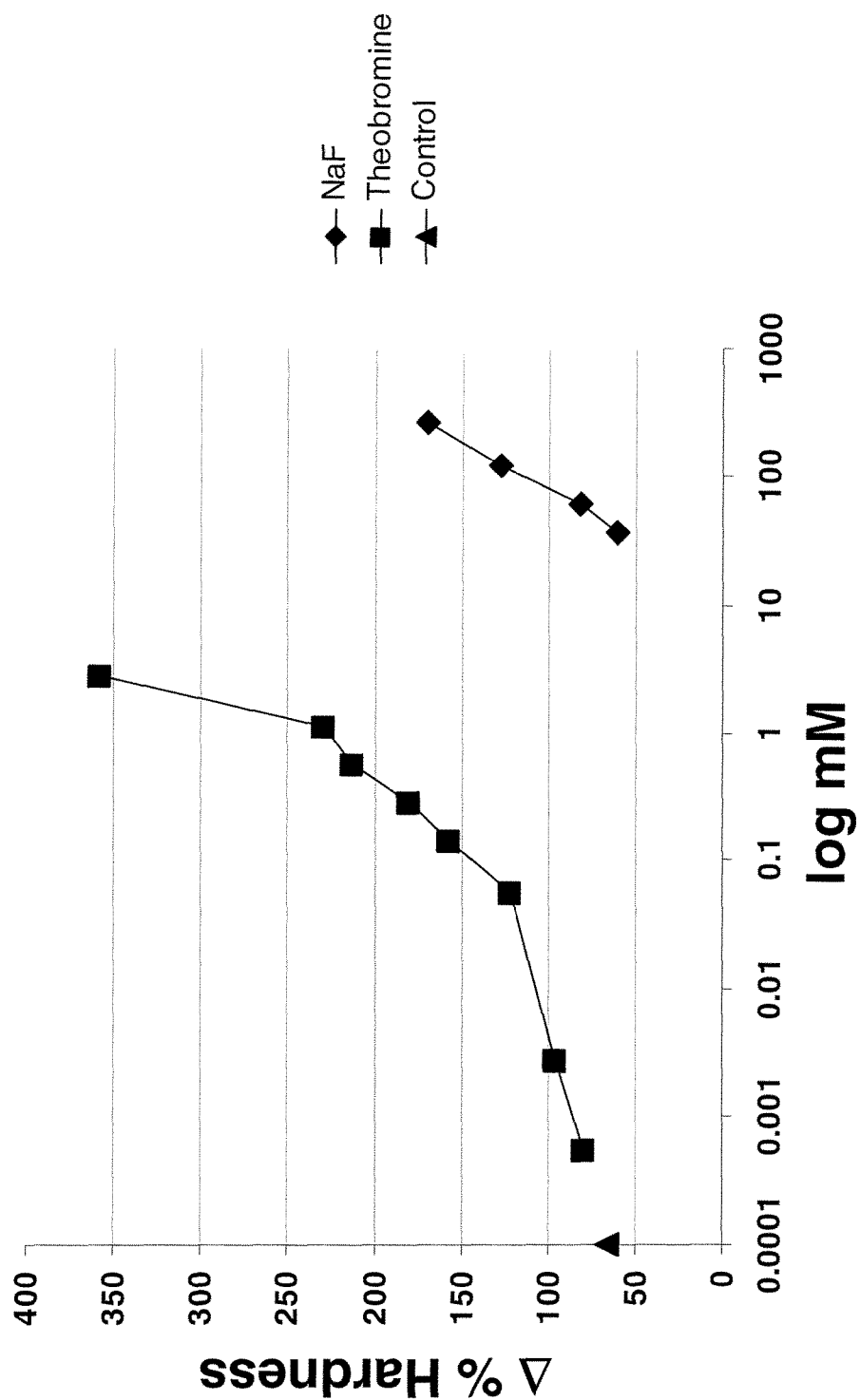
FIG. 11 is a semi-log scatterplot showing the effects of different concentrations of NaF and theobromine on microhardness.

The surprising and unexpected effectiveness of the disclosed theobromine composition is further demonstrated in the semi-logarithmic plot of FIG. 11, in which the molarity of the sodium fluoride and the theobromine solutions from FIG. 10 is shown along the X-axis (plotted on a logarithmic scale). FIG. 11 shows clearly that the theobromine composition is significantly more effective than sodium fluoride, on a molecule-to-molecule basis, at enhancing the indentation hardness of teeth.

Example 4

Comparison of Theobromine and NaF on Scratched Human Teeth

Figure 12:
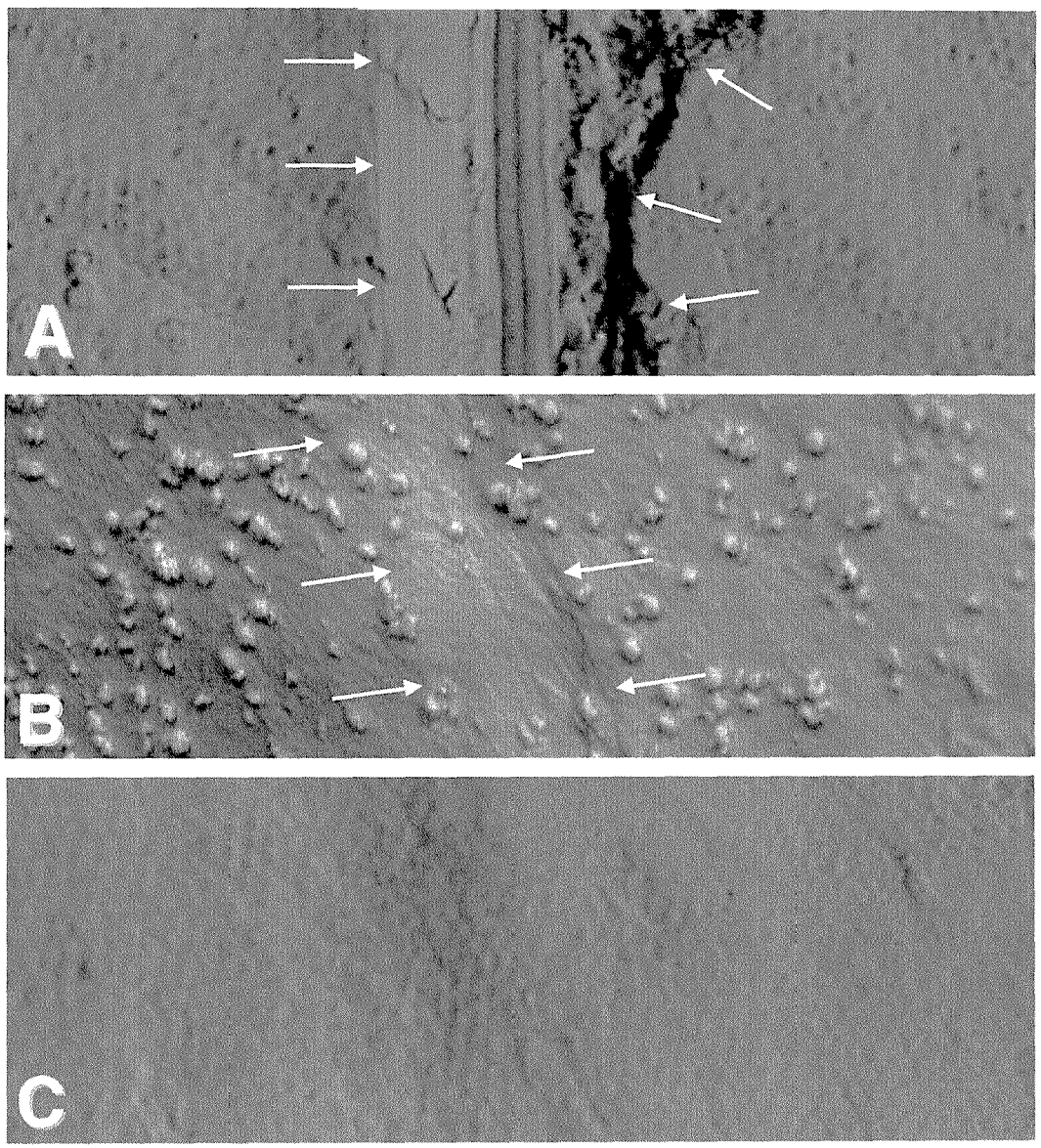
FIG. 12 shows three scanning electron micrograph of three different tooth samples scratched with a diamond scribe.
Figure 13:
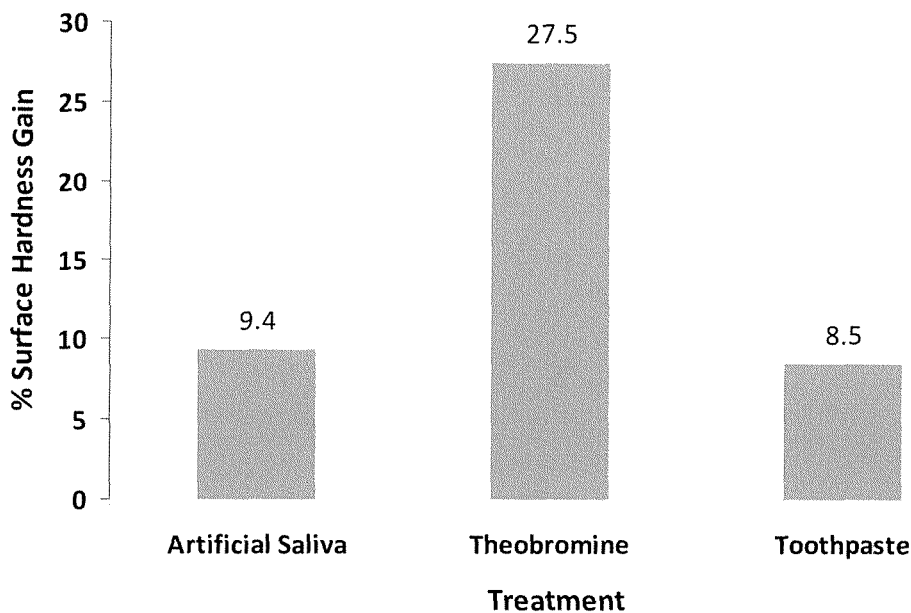
FIG. 13 is a bar graph showing the change in Vickers microhardness of tooth samples subjected to a caries model, then incubated for 14 days to artificial saliva, 0.25% NaF toothpaste, or 200 mg/L theobromine.
Figure 14:
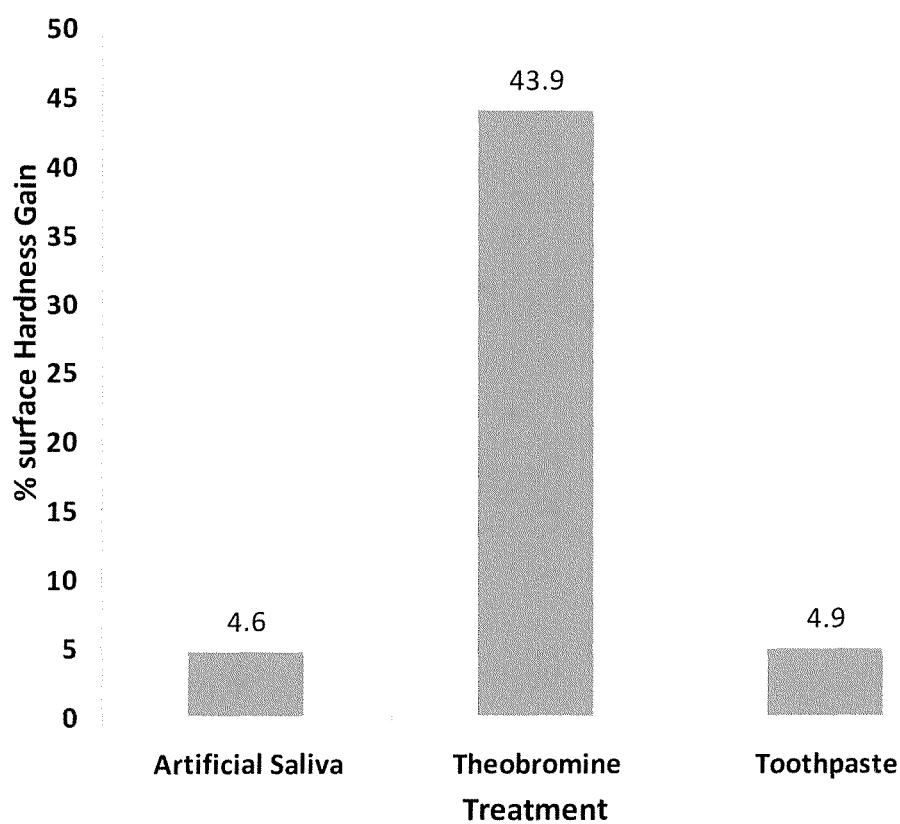
FIG. 14 is a bar graph showing the change in Vickers microhardness of tooth samples subjected to an erosion model, then incubated for 14 days to artificial saliva, 0.25% NaF toothpaste, or 200 mg/L theobromine.

Isolated human teeth were scratched with a diamond scribe on the enamel surface. Each tooth was then etched for 15 seconds in 0.1 M HCl, rinsed with distilled water, then exposed for 15 seconds to a 0.1 M oxalic acid solution, and then rinsed once more with distilled water. The teeth were then placed into a 0.2 M Na$_2$HPO$_4$ solution, to which either theobromine (to a final concentration of 200 mg/L), NaF (to a final concentration of 0.25%), or water (control) was added. The pH was adjusted to 7.4-7.6, after which a 0.2 M CaCl$_2$ solution was added with stirring (the solution turns immediately turbid from Ca-phosphate precipitation). The pH was checked and adjusted immediately to between 7.4 and 7.6, as required. As noted above, the final concentrations of theobromine and NaF were 200 mg/L and 0.25%, respectively. A volume ratio of about 3:5 Na$_2$HPO$_4$ solution-to-CaCl$_2$ solution was used to avoid any excess of either Ca or P. The teeth were so incubated at room temperature for about 90 minutes, after which they were removed from solution, carefully rinsed several times with distilled water, and then dried in a desiccator for 24 hours. After drying, the teeth were carbon-coated for viewing via scanning electron microscopy (SEM). The SEM results are shown in FIGS. 12-14, and discussed below.

FIG. 12A shows a scratched tooth that was incubated for 90 minutes in control solution (no theobromine or NaF). The scratch produced by the diamond scribe, shown by the arrows, proceeds from the top of the figure to the bottom, and is deep and pronounced. FIG. 12B shows a scratched tooth that was incubated for 90 minutes in the presence of 0.25% NaF. The scratch produced by the diamond scribe appears to be partly-filled, as shown by the arrows pointing to the shadow on the tooth surface, yet the scratch remains wide. The teeth incubated with NaF also demonstrated small, focused mineral deposits over the entire visible surface. In marked contrast to both the control and the NaF experiments, FIG. 12C shows a scratched tooth that was incubated for 90 minutes in the presence of 200 mg/L theobromine. The scratch produced by the diamond scribe (approximate position shown by the arrows) is almost completely obscured by a smooth layer of freshly-deposited calcium phosphate.

Example 5

Calcium Phosphate Deposition: Theobromine vs. NaF

Using a dental drill, holes were drilled into the enamel surfaces of isolated human teeth, with each tooth receiving three holes in three separate locations. After drilling, the teeth were incubated in solutions as disclosed in EXAMPLE 4, except that an additional set of teeth was incubated in the presence of 200 mg/L and 0.25% NaF. After desiccation, each tooth was cut to enable visualization of the drilled holes and measure the amount of calcium phosphate deposition in said holes. The teeth were visualized via SEM, as in EXAMPLE 4, and the amount of calcium phosphate deposition measured for each experimental condition.

As shown by TABLE 3 below, all treatments yielded a statistically significant increase in the amount of calcium phosphate deposited versus control. While dual incubation with NaF and theobromine yielded a higher mean amount of calcium phosphate deposited, it was not significantly different from that achieved with NaF alone. Surprisingly, incubation with theobromine alone produced a statistically significant increase in the amount of calcium phosphate deposited over all other conditions tested.

TABLE 3

| Incubation Condition | Calcium Phosphate ($\mu$m) ± S.D. |
| --- | --- |
| control | 54 ± 6.1 |
| NaF (0.25%) | 70 ± 8.8 |
| Theobromine (200 mg/L) | 87 ± 5.5 |
| NaF (0.25%) + Theobromine (200 mg/L) | 84 ± 7.6 |

Example 6

Comparison of Theobromine and NaF in a Caries Model

The anticaries potential of theobromine-containing toothpaste formulations was compared to a standard NaF dentifrice by determining the early caries lesion remineralization in an established in vitro remineralization/demineralization pH cycling model.

Production of Artificial Caries-Like Lesions

Following consent from human donors, freshly extracted human molar teeth were collected from various clinics of the Dental School of the University of Texas Health Science Center at San Antonio (UTHSCSA). The teeth were cleaned of debris/stains, and examined with a transilluminator. Teeth without caries or enamel malformations were selected and cleaned with pumice to remove the remnants of pellicle from the buccal surface. Using a water-cooled diamond wire saw, 3 tooth blocks were produced from each of 30 teeth used, with each block measuring approximately 3 mm length×2 mm width×1.5 mm thickness. Then using plain back diamond lapping film (1 $\mu$m) in a MultiPrep™ Precision Polishing machine (Allied High Tech, USA), the enamel surface of each block was polished to achieve a flat surface. Following this, all surfaces of each block were painted with two coats of acid-resistant nail varnish, except buccal surface. Then, an early caries-like lesion was created on this exposed buccal surface on each block by 7 days of demineralization in an acidified gel system as described by Amaechi B T, Higham S M, Edgar W M. "Factors affecting the development of carious lesions in bovine teeth in vitro" *Archives of Oral Biology* 1998; 43:619-628 (incorporated by reference in its entirety). The gel was prepared by adding 0.10 M sodium hydroxide to 0.10 M lactic acid to give a final pH value of 4.5. To this solution, 6% w/v hydroxyethyl cellulose was added whilst vigorously stirring. The final consistency of gel achieved exhibited a viscosity in the region of 100 cP.

Following lesion formation, the nail varnish was carefully and totally removed with acetone. Thus, a total of 3 lesion-bearing blocks were obtained from each tooth (30 teeth) to be used for the remineralization test (a total of 90 blocks).

Treatment Procedure

The 3 blocks from each tooth were assigned randomly to three treatment groups (n=30, per treatment group) based on the three dentifrices to be tested: Group 1: Control toothpaste (neither fluoride nor theobromine); Group 2: standard NaF toothpaste (e.g., Colgate, Crest regular) containing 0.243% NaF; and Group 3: Theobromine toothpaste containing 200 mg/L theobromine. The 30 blocks for each treatment group were distributed into 3 subgroups of 10 blocks each. Using an acid-resistant nail varnish, the 10 blocks for each subgroup were stuck onto a cylindrical rod attached to the cover of a 30-mL color-coded treatment vial, giving a total of three vials for each dentifrice group.

The remineralization study was conducted using a pH cycling (demineralization/re-mineralization) model, simulating the activities within the oral environment as closely as possible (see TABLE 4). Pooled human saliva was used as the remineralization medium in all treatment regimens, while the acidified gel described above for the development of the early caries lesion was used as the acid challenge medium. Fresh, pooled human saliva was used each day. Standard slurry of the dentifrices was prepared by mixing 1 part dentifrice and 3 parts pooled human saliva (9 g: 27 mL) using a laboratory stand mixer, until homogenous. Fresh slurry for each group was prepared just prior to each treatment episode. The cyclic treatment regimen for each day consisted of three 1-hour acid challenges, three 2-minute dentifrice treatment periods, and then saliva treatment for the rest of the time, as shown in the treatment schedule below at TABLE 4 (Day 1 was an all-day saliva treatment to allow for development of pellicle; treatment on subsequent days was as given in TABLE 4).

TABLE 4

| Start Time | End Time | Treatment |
| --- | --- | --- |
| 8:00 | 9:00 | Acid challenge |
| 9:00 | 9:02 | Dentifrice treatment |
| 9:02 | 12:00 | Saliva treatment |
| 12:00 | 13:00 | Acid challenge |
| 13:00 | 13:02 | Dentifrice treatment |
| 13:02 | 16:00 | Saliva treatment |
| 16:00 | 17:00 | Acid challenge |
| 17:00 | 17:02 | Dentifrice treatment |
| 17:02 | 8:00 (next day) | Saliva treatment |

For treatment, 15 mL of the treatment medium (pooled human saliva, dentifrice slurry or acidified gel) was placed into each color-coded 30 mL treatment vial. All treatments were stirred at 350 rpm. The pH of each product (one slurry) was measured once daily before treatment. After treatment with one medium, the specimens were rinsed with running deionized water, and dried with a paper towel before immersion into the next agent. The daily regimen was repeated for 14 days, after which 10 blocks from each of the three groups were removed for Vickers microhardness testing as described below.

The remaining 20 blocks from each of the three groups (n=60) will continue to be treated according to the treatment schedule of TABLE 4 for a total of 28 days, and will be evaluated as described under "Baseline Transverse Microradiographic (TMR) Data Analysis" and "Post Treatment Processing."

Vickers Microhardness Analysis

Vickers microhardness tests were performed on each sample (3 groups of 10 blocks each, 30 total), using a diamond indenter having the form of a right pyramid to indent the test material. The Vickers microhardness of each of these blocks was measured prior to the Treatment Procedure above, and again after being subjected to the Treatment Procedure for 14 days. The diamond indenter pyramid had a square base and an angle of 136° between opposite faces, and was subjected to a load of 25 gf (gram-force) for 15 seconds dwelling time. The force applied was roughly perpendicular to the enamel surface. When finished, the diamond tip retracted automatically, and the lengths of the two diagonals produced by the tip, apparent on the enamel surface of each sample, was measured via scanning electron microscopy, and their average calculated. The Vickers hardness (HV) was calculated by dividing the gf load (in kgf) by the square mm area (mm$^2$) of indentation according to Formula 2, where F=load (kgf) and d=the average of the two diagonals (mm).

$$HV = \frac{2F\sin\frac{136°}{2}}{d^2} = \text{approximately } 1.854\frac{F}{d^2} \quad \text{Formula 2}$$

As shown in FIG. 13, blocks subjected to the caries model and then treated for 14 days with theobromine toothpaste demonstrated dramatically improved HV (surface hardness gain of 27.5%) compared to blocks treated for 14 days with either artificial saliva (control) or NaF toothpaste (surface hardness gains of 9.4% and 8.5%, respectively).

Baseline Transverse Microradiographic (TMR) Data Analysis

A tooth slice (~150 μm thick) will be cut from each lesion-bearing tooth block using a water-cooled diamond wire saw. This slice will serve as a baseline to be used to determine the Pre-treatment TMR parameters (mineral loss (AZ) and lesion depth (LD)) of the lesion before remineralization (pretest parameters). Also the parameters of the control slices will be used to select the lesions that are suitable for the remineralization study. The baseline slices will be processed for TMR assessment as follows. First, both sides of the slice will be polished using Adhesive Back lapping film in a MultiPrep™ Precision Polishing machine (Allied High Tech, USA) to achieve planoparallel surfaces as well as reduce the thickness of the slice to 100 μm (the appropriate thickness for TMR). Following this, the slices will be microradiographed on type 1A high resolution glass X-ray plates (Microchrome Technology, CA, USA) using a Phillips x-ray generator system set up for this purpose. The plates will be exposed for 10 minutes at an anode voltage of 20 kV and a tube current of 10 mA, and then processed. Processing will consist of a 5 minute development in Kodak HR developer and 15 min fixation in Kodak Rapid-fixer before a final 30 minute wash period. After drying, the microradiographs will be subjected to visualization and image analysis using a computer program (TMR2006 version 3.0.0.6). The hardware will be a Leica DMR optical microscope linked via a Sony model XC-75CE CCTV camera to a personal computer. The enhanced image of the microradiograph will be analyzed under standard conditions of light intensity and magnification and processed, along with data from the image of the step wedge, by the TMR program. By this method, the parameters of integrated mineral loss (ΔZ, vol %. μm) and lesion depth (LD, μm) will be quantified for each carious lesion.

Post-Treatment Processing

After treatment for 28 days, a tooth slice (~150 μm thick) will be cut from each of the 60 blocks and processed for microradiography as described above for the control specimen. Although the control slices will have been microradiographed and analyzed for selection of the appropriate lesions, they will be microradiographed again together with the post-test slices and both will be analyzed together for quantification of ΔZ and LD as described for control sections above. This will enable both groups to be microradiographed and analyzed under the same conditions. This process will yield the following information: 1) the pre-test TMR parameters ($\Delta Z_1$ and LD1) of the lesions; 2) the post-test TMR parameters ($\Delta Z_2$ and LD2) of the lesions; and 3) the pre-test and post-test TMR images of the lesions.

Data Handling and Interpretation

The mean (n=20) values of the lesion parameters, mineral loss [ΔZ (vol %. μm)] and lesion depth [LD (μm)], will be calculated for the pre- and post-test groups of each of the three treatment dentifrices. The following examinations will be carried out with the data and the images: A) using the TMR images, the pattern and the extent of remineralization produced within the internal structure of each lesion by each treatment method will be examined and described. This will be clearly shown by comparing the pre- and post-test images side-by-side; and B) the mean values of the pre-test and post-test lesion parameters (ΔZ and LD) for each test product will be compared to determine any significant change (remineralization) made by the test product. However, to make comparisons between the three test groups, the percentage change in lesion parameters calculated relative to the control will be determined for each test product (Percentage change will be used for ranking and comparison in order to make provision for the fact that although the three blocks will come from the same tooth, the lesion parameters for the blocks may differ at baseline). This is calculated according to Formulae 3 and 4:

$$\% \text{ change in } \Delta Z = \frac{\Delta Z_1(\text{control}) - \Delta Z_2(\text{test})}{\Delta Z_1(\text{control})} \times 100 \quad \text{Formula 3}$$

$$\% LD = \frac{LD_1(\text{control}) - LD_2(\text{test})}{LD_1(\text{control})} \times 100 \quad \text{Formula 4}$$

Statistical Power Analysis

The power analysis will be performed using nQuery Advisor software (Statistical Solutions, Cork, Ireland) and will be based on previous results obtained by Amaechi BT. "Pattern of the Effect of Fluoride Varnishes On Early Caries"

*J. Dent Res.* 2008; 87(Special Issue B):abst. 1195 (incorporated by reference in its entirety).

Example 7

Comparison of Theobromine and NaF in an Erosion Model

The anticaries potential of theobromine-containing toothpaste formulations will be compared to a standard NaF dentifrice by determining the early caries lesion remineralization in an established in vitro remineralization/demineralization pH cycling model.

Production of Artificial Erosion Lesions

Following consent from human donors, freshly extracted human molar teeth were collected from various clinics of the Dental School of the University of Texas Health Science Center at San Antonio (UTHSCSA). The teeth were cleaned of debris/stains, and examined with a transilluminator. Teeth without caries or enamel malformations were selected and cleaned with pumice to remove the remnants of pellicle from the buccal surface. Using a water-cooled diamond wire saw, 3 tooth blocks were produced from each of 30 teeth to be used, with each block measuring approximately 3 mm length×2 mm width×1.5 mm thickness. Then, using plain back diamond lapping film (1 μm) in a MultiPrep™ Precision Polishing machine (Allied High Tech, USA), the enamel surface of each block was polished to achieve flat surface.

Following this, all surfaces of each block were painted with two coats of acid-resistant nail varnish, except buccal surface. Using acid-resistant nail varnish the 90 tooth blocks were attached to 9 glass slides (10 blocks/slide). Each block-bearing glass slide was immersed in a 50 mL beaker containing freshly prepared 1% citric acid (1.0 g of powdered citric acid anhydrous dissolved in 100 mL of deionized distilled water under constant agitation with magnetic stirrer) for 10 minutes with continuous agitation with magnetic stirrer. After immersion for the designated time, specimens were removed from the solution and rinsed thoroughly with distilled water for 10 seconds. Specimens were then dried carefully with paper towels and removed from the glass slide, providing a total of 3 lesion-bearing blocks from each tooth for the remineralization tests.

The Treatment Procedure was performed as described above for EXAMPLE 6. As in EXAMPLE 6, ten blocks from each of three treatment groups (control, NaF toothpaste, and theobromine toothpaste) were removed after immersion for 14 days and subjected to Vickers microhardness testing as described above in EXAMPLE 6.

The remaining 20 blocks from each of the three groups (n=60) will continue to be treated according to the treatment schedule of TABLE 4 for a total of 28 days, and will be evaluated as described under "Baseline Transverse Microradiographic (TMR) Data Analysis" and "Post Treatment Processing" in EXAMPLE 6 above; for these 20 blocks, the Baseline Transverse Microradiographic (TMR) Data Analysis, the Post-Treatment Processing, the Data Handling and Interpretation, and the Statistical Power Analysis will all be performed as described above for EXAMPLE 6.

As shown in FIG. 14, blocks subjected to the erosion model and then treated for 14 days with theobromine toothpaste demonstrated dramatically improved HV (surface hardness gain of 43.9%) compared to blocks treated for 14 days with either artificial saliva (control) or NaF toothpaste (surface hardness gains of 4.6% and 4.9%, respectively).

All references cited in this specification are herein incorporated by reference as though each reference was specifically and individually indicated to be incorporated by reference. The citation of any reference is for its disclosure prior to the filing date and should not be construed as an admission that the present application is not entitled to antedate such reference by virtue of prior invention.

It will be understood that each of the elements described above, or two or more together may also find a useful application in other types of methods differing from the type described above. Without further analysis, the foregoing will so fully reveal the gist of the present application that others can, by applying current knowledge, readily adapt it for various applications without omitting features that, from the standpoint of prior art, fairly constitute essential characteristics of the generic or specific aspects of this application set forth in the appended claims. The foregoing embodiments are presented by way of example only; the scope of the present application is to be limited only by the following claims.

We claim:

1. A method of enhancing the indentation hardness of at least one tooth of a mammal in need thereof, said method comprising:
    a) providing a composition comprising (i) from about 1 mg/L to about 500 mg/L of theobromine, theobromine salt, or theobromine double salt, (ii) at least one source of calcium, and (iii) at least one source of phosphate, wherein the pH of said composition is about 6.0 to about 8.5; and
    b) topically administering said composition to said at least one tooth of said mammal,
    wherein said composition is selected from the group consisting of a toothpaste, a mouthwash, dental floss, a coated dental strip, a dental varnish, a dental cement, a dental adhesive, a dental polishing paste, a tooth-bleaching agent, a cavity-filling material, a dental resin, and a chewing gum.

2. The method of claim 1, wherein said at least one source of calcium is selected from the group consisting of calcium chloride, calcium carbonate, calcium gluconate, calcium phosphate, and combinations thereof.

3. The method of claim 1, wherein said at least one source of phosphate is selected from the group consisting of potassium dihydrogen phosphate, dipotassium hydrogen phosphate, tripotassium phosphate, sodium dihydrogen phosphate, disodium hydrogen phosphate, trisodium phosphate, and combinations thereof.

4. The method of claim 1, further comprising at least one isotonic agent.

5. The method of claim 4, wherein said isotonic agent is a polyhydric alcohol.

6. The method of claim 5, wherein said polyhydric alcohol is selected from the group consisting of xylitol, sorbitol, mannitol, maltitol, lactitol, isomalt, erythritol, arabitol, glycerol, and combinations thereof.

7. The method of claim 1, wherein said composition further comprises at least one thickener.

8. The method of claim 7, wherein said thickener is selected from the group consisting of methyl cellulose, carboxymethyl cellulose, ethyl cellulose, hydroxypropyl cellulose, and combinations thereof.

9. The method of claim 1, wherein said composition further comprises an antibacterial agent, an antimicrobial agent, or combinations thereof.

10. The method of claim 9, wherein said antibacterial agent is selected from the group consisting of triclosan, hydrogen peroxide, methyl-4-hydroxybenzoate, clove oil, and combinations thereof.

11. The method of claim 1, for enhancing the hardness of at least one tooth, wherein said composition enhances said hardness more than a dentifrice containing 0% to about 1.1% of either sodium fluoride or sodium monofluorophosphate.

12. The method of claim 11, wherein said composition enhances said hardness more than a dentifrice containing 0% to about 0.5% of sodium fluoride or 0% to about 0.76% sodium monofluorophosphate.

13. The method of claim 11, wherein said composition enhances said hardness more than a dentifrice containing 0% to about 0.25% of sodium fluoride or 0% to about 0.76% sodium monofluorophosphate.

14. The method of claim 11, wherein said composition enhances said hardness more than a dentifrice containing 0% to about 0.15% of sodium fluoride or 0% to about 0.76% sodium monofluorophosphate.

15. The method of claim 1, wherein said enhancing further comprises deposition of new hydroxylapatite and/or calcium phosphate onto said tooth.

\* \* \* \* \*